(12) United States Patent  
Villazón-Terrazas et al.

(10) Patent No.: US 11,127,502 B2  
(45) Date of Patent: Sep. 21, 2021

(54) COMPUTER APPARATUS AND METHOD TO IDENTIFY HEALTHCARE RESOURCES USED BY A PATIENT GIVEN A POTENTIAL DIAGNOSIS

(71) Applicant: Fujitsu Limited, Kawasaki (JP)

(72) Inventors: Boris Villazón-Terrazas, Madrid (ES); Nuria Garcia Santa, Madrid (ES); Victor De La Torre, Madrid (ES)

(73) Assignee: FUJITSU LIMITED, Kawasaki (JP)

( * ) Notice: Subject to any disclaimer, the term of this patent is extended or adjusted under 35 U.S.C. 154(b) by 541 days.

(21) Appl. No.: 15/695,438

(22) Filed: Sep. 5, 2017

(65) Prior Publication Data

US 2018/0101654 A1    Apr. 12, 2018

(30) Foreign Application Priority Data

Oct. 6, 2016    (DE) .......................... 102016219430.5

(51) Int. Cl.
*G06Q 10/00* (2012.01)
*G16H 50/20* (2018.01)
(Continued)

(52) U.S. Cl.
CPC ......... *G16H 50/20* (2018.01); *G06Q 10/0631* (2013.01); *G16H 10/60* (2018.01);
(Continued)

(58) Field of Classification Search
CPC ........ G16H 50/20; G16H 40/20; G16H 10/60; G16H 50/30; G16H 40/63; G16H 50/50;
(Continued)

(56) References Cited

U.S. PATENT DOCUMENTS 5,991,728 A    11/1999 DeBusk et al.
6,581,204 B2 *    6/2003 DeBusk ................ G06F 19/324
                                                    717/120
(Continued)

FOREIGN PATENT DOCUMENTS

JP    2009-205654 A    9/2009
JP    2014-228907 A    12/2014
(Continued)

OTHER PUBLICATIONS

German Search Report dated Feb. 8, 2017 in German Patent Application No. 102016219430.5.
(Continued)

*Primary Examiner* — Maroun P Kanaan
(74) *Attorney, Agent, or Firm* — Staas & Halsey LLP

(57) ABSTRACT

A computer apparatus to identify healthcare resources used by a patient given a potential diagnosis, the apparatus comprising: a memory storing instructions for execution by a processor, the processor configured by the instructions to implement an impact estimator to: receive a patient clinical object, PCO, which represents the patient in the form of a graph, and includes previous healthcare resource utilization, HCRU, information of the patient as a patient HCRU subgraph; receive an HCRU knowledge graph, HCRU KG, associating healthcare resources with medical services; receive potential diagnosis information from a clinician; identify and extract potential healthcare resources and services in the HCRU KG associated with the potential diagnosis to form an HCRU subgraph associated with the potential diagnosis; and to perform graph analysis on the HCRU subgraph associated with the potential diagnosis and the patient HCRU subgraph to obtain an updated patient HCRU subgraph taking the potential diagnosis into account.

12 Claims, 22 Drawing Sheets

(51) Int. Cl.
  *G06Q 10/06* (2012.01)
  *G16H 20/40* (2018.01)
  *G16H 50/50* (2018.01)
  *G16H 40/63* (2018.01)
  *G16H 50/70* (2018.01)
  *G16H 40/20* (2018.01)
  *G16H 10/60* (2018.01)
  *G16H 50/30* (2018.01)
  *G06Q 50/22* (2018.01)

(52) U.S. Cl.
  CPC .............. *G16H 20/40* (2018.01); *G16H 40/20* (2018.01); *G16H 40/63* (2018.01); *G16H 50/30* (2018.01); *G16H 50/50* (2018.01); *G16H 50/70* (2018.01); *G06Q 50/22* (2013.01)

(58) Field of Classification Search
  CPC ........ G16H 50/70; G16H 20/40; G16H 10/20; G16H 20/10; G16H 15/00; G06Q 50/22; G06Q 10/0631; G06Q 10/04; G06F 16/9024; G06F 9/4406
  See application file for complete search history.

(56) References Cited

U.S. PATENT DOCUMENTS

| | | |
|---|---|---|
| 7,702,522 B1 | 4/2010 | Sholem |
| 8,271,295 B1 | 9/2012 | Miller et al. |
| 2003/0065534 A1 | 4/2003 | McCartney |
| 2006/0074720 A1* | 4/2006 | Brutting ................. G06Q 50/22 705/3 |
| 2009/0089092 A1 | 4/2009 | Johnson et al. |
| 2012/0173253 A1 | 7/2012 | Reynolds et al. |
| 2014/0236625 A1* | 8/2014 | Hartman ................. G06Q 50/01 705/3 |
| 2014/0278454 A1 | 9/2014 | Peled |
| 2014/0344274 A1 | 11/2014 | Kido et al. |
| 2016/0253687 A1 | 9/2016 | Wei et al. |
| 2016/0283880 A1 | 9/2016 | Jin |
| 2017/0083673 A1* | 3/2017 | Dawson, III ........... G16H 10/60 |

FOREIGN PATENT DOCUMENTS

| | | | |
|---|---|---|---|
| WO | 99/41653 | 8/1999 | |
| WO | 2005/111902 | 11/2005 | |
| WO | WO-2016054043 A1 * | 4/2016 | ........... G06F 19/324 |

OTHER PUBLICATIONS

European Search Report dated Jul. 24, 2017 in European Patent Application No. 17166979.9.

Hu Z, et al. "Online Prediction of Health Care Utilization in the Next Six Months Based on Electronic Health Record Information: A Cohort and Validation Study" J Med Internet Res 2015;17(9):e219, 15 pages**.

Notice of Reasons for Refusal dated Aug. 3, 2021 in corresponding Japanese Patent Application No. 2017-188642 (4 pages) (3 pages English Translation).

* cited by examiner

FIG. 4

Model for healthcare services     Model for healthcare resources

COMPUTER APPARATUS AND METHOD TO IDENTIFY HEALTHCARE RESOURCES USED BY A PATIENT GIVEN A POTENTIAL DIAGNOSIS

CROSS-REFERENCE TO RELATED APPLICATIONS

This application claims the benefit of German Application No. 102016219430.5, filed Oct. 6, 2016, in the German Intellectual Property Office, the disclosure of which is incorporated herein by reference.

Background

The embodiments relate to potential medical resource utilization by an individual or a living subject, usually referred to as a patient, when there is a new diagnosis. The patient may be a human or potentially an animal, such as a specimen of a rare breed or even a pet. The patient is of a medical institution, such as a hospital, or doctor's, dentist's or veterinarian's practice. The term medical institution can also cover a medical conglomeration across different locations and hospital/practices.

In many scenarios, the patient may already be suffering from a disorder, but in others the patient is currently healthy, and thus the term medical condition includes conditions such as pregnancy, as well as disorders, illnesses and diseases. The embodiments are thus widely applicable in provision of healthcare and veterinary healthcare.

Resource utilization is the amount of a good or service consumed or the pattern of use of a good or service within a specified time period. Quality care remains the goal in healthcare and outcome-focused plans of care have been shown to contain resource utilization and enhance quality. The success of quality care services depends on good coordination and management of the health care resources utilization in the medical institutions.

One of the most fundamental problems related to population health is the rising healthcare costs. In recent years, many organizations have begun to measure and track health care costs. This process involves a mix of complicated factors, including patient illness burden, market-specific variation, service utilization, and negotiated prices.

Health care spending represented 17.9 percent of the US gross domestic product (GDP) in 2012, and it is expected to continue to rise over 20 percent by 2018. Rising costs prohibit thousands from being able to afford treatment, and contribute largely to personal bankruptcies. Consequently, affordability of care has become an increasingly prominent issue.

Although public and private payers express considerable interest in calculating the value of health care services, it remains a challenge to develop and implement nationally accepted measures. Expenditure prediction models typically incorporate information on clinical conditions based on data from medical records. Some of the approaches to this are (1) the relative risk or risk ratio (RR), (2) the Diagnostic Cost Group (DCG) model, (3) the Medical Episode Grouper (MEG) methodology, (4) and episode treatment group (ETG) methodology.

Several differences among resource use measures could guide a community collaborative's choice of measures. Many resource measures focus on hospitals, including simple measures such as a mean length of stay and more complex multiple-output measures using econometric or mathematical programming techniques.

According to an embodiment of a first aspect, there is provided a computer apparatus to identify healthcare resources used by a patient given a potential diagnosis, the computer apparatus comprising:
a memory storing instructions for execution by a processor, the processor configured by the instructions to implement an impact estimator to:
receive a patient clinical object, PCO, which represents the patient in the form of a graph, and includes previous healthcare resource utilization, HCRU, information of the patient as a patient HCRU subgraph;
receive an HCRU, knowledge graph, HCRU KG, associating healthcare resources with medical services;
receive potential diagnosis information from a clinician;
identify and extract potential healthcare resources and services in the HCRU KG associated with the potential diagnosis to form an HCRU subgraph associated with the potential diagnosis; and to
perform graph analysis on the HCRU subgraph associated with the potential diagnosis and the patient HCRU subgraph to obtain an updated patient HCRU subgraph taking the potential diagnosis into account.

Embodiments provide a way of estimating potential resource utilization of healthcare resources for a patient.

The inventors have found a way of identifying potential healthcare utilization which is tailored to the patient and potentially also to the medical institution concerned but which also incorporates a standard framework using open data (for example in the form of one or more publically available healthcare and/or medical services databases) and clinician input, which can act to standardize the results across a population of patients.

All of the aforementioned approaches in the prior art focus directly on calculating the associated costs instead of concentrating first on the resource utilization. One idea behind the embodiments is to derive and focus on health care resource utilization.

SUMMARY

In summary, within the healthcare domain, the inventors believe that
there are no standards for representing health care resource utilization, in the same way as there are standards for diseases, e.g., ICD9; there are only plain lists of health care resources and they are specific to a particular area or region;
there are no works that associate DRG's to medical resources and services;
there are no ways to specialize the plain lists of health care resources to the specific needs and reality of a particular hospital institution;
there is a lack of methods and tools that exploit information about healthcare resource utilization and its association to patient clinical data.

The inventors have come to the conclusion that to achieve good management in health care services it is important to have a standardization which collects and links (a hierarchy of) the different medical services with resources usage. A graph presentation of this standardization is practical for further manipulation and understanding. Moreover, this model should be associated to the specific needs and reality of each medical institution, when possible. This task can leverage semantic technologies and knowledge graph tools to get the benefits of this approach, such as semantic linking and annotating, semantic alignment with external resources, straight publishing and sharing process to establish standards protocols, etc.

The impact estimator can use graph-based mining to estimate how the HCRU subgraph associated with the potential diagnosis will affect the patient HCRU subgraph.

Vertices in the updated patient HCRU subgraph associated with the potential diagnosis may be provided with scores related to the probability of the resource utilization and use of the medical services.

The embodiments are not limited in application to a single patient, but can be used to assess healthcare resource utilization of a population of patients. In one embodiment, the computer apparatus is to identify healthcare resources potentially used by a population of patients (for example of a medical institution). In this case the impact estimator can receive a PCO for each patient of the patient population. The sum of the updated patient HCRU subgraphs can then be used to estimate potential healthcare resource utilization across the population.

The PCO may be provided as a graph centered on a patient ID vertex, with edges linking the patient ID vertex to vertices representing clinical data, and (directly or indirectly) linking to vertices representing resource utilization and medical services. These service and resource vertices form the patient HCRU subgraph.

The PCO may be limited (by the user or automatically) to one or more of: a condition, an episode of a condition, a timeframe, and a diagnosis. This allows the original and updated HCRU subgraphs (and their analysis) to be more specific The potential diagnosis information can include a diagnosis and any relations it may have to symptoms, drugs, and treatments. This allows easier matching with the HCRU KG.

The HCRU KG and PCO (with its subgraph) may be provided by one or more other systems. However in some embodiments, the processor is further configured to provide: a healthcare resource utilization, HCRU, knowledge graph, KG, builder; and a patient HCRU engine; wherein:

the HCRU KG builder is arranged to input open data and clinician information, to generate a set of medical services terms and a set of medical resources terms from the open data and clinician information, and to associate the medical resources with the medical services to build the general HCRU KG; and the patient HCRU engine is arranged to input a patient clinical object, PCO, which represents the patient in the form of a graph, and to use the HCRU KG to associate and annotate the PCO with previous healthcare resource utilization information.

The computer apparatus may further comprise an HCRU KG customizer wherein:

the HCRU KG customizer is arranged to match the HCRU KG with records of the medical institution to provide a customized subgraph of the HCRU KG which is specific to the medical institution; and the patient HCRU engine is arranged to use the customized subgraph part of the HCRU KG to associate and annotate the PCO with previous healthcare resource utilization information. This allows the data in the HCRU KG and subgraphs to be specific to a certain medical institution and have a more practical use for that institution.

The HCRU KG builder may be configured to collect seeds for an initial set of medical services terms and for an initial set of medical resources terms from the clinician information; and to reconcile the collected initial sets of terms from the clinician with the open data to provide an enhanced set of terms proposed by the clinicians and annotated using the open data. The HCRU KG builder may then create two models, one representing healthcare resources and the other representing healthcare services; and create relations between the two models, using relation mining in the open data, scoring the relations according to the number of occurrences of the relations in the open data. The occurrence scoring can use any suitable methodology, usually based on co-occurrence of the terms in the same dataset or within a predefined distance in the same dataset for example.

The HCRU KG customizer functions to fit the medical institution and HCRU KG data together. The HCRU KG customizer may customize the HCRU KG by any of: identifying services of the medical institution that are represented in the HCRU KG; filtering out services in the HCRU KG that are not provided in the medical institution; and identifying what resources are used from medical institution data and removing resources from the HCRU KG that are not available in the medical institution.

The HCRU KG customizer may use process mining to discover how resources are used in the medical institution (in terms of what services use what resources) and to adapt the HCRU KG to the particular way that resources are used in the medical institution.

The HCRU KG customizer may input an electronic medical institution log and internal regulations of the medical institution. It can then extract process knowledge from the electronic medical institution log (using known process mining techniques) and project the extracted process knowledge onto the internal regulations of the medical institution to check if the extracted process knowledge conforms to the internal regulations of the medical institution.

The patient HCRU engine can use any suitable methodology to add the resource data to the PCO. It may use clinical data present in the PCO and add links to new vertices representing healthcare resources using the customized subgraph of the HCRU KG as a template (for instance by using the links in the HCRU KG between services and resources to link the same or similar services in the PCO to new resources, which are taken from the corresponding position in the HCRU KG).

According to an embodiment of a second aspect, there is provided a computer-implemented method to identify healthcare resources used by a patient given a potential diagnosis, the method comprising:

receiving a patient clinical object, PCO, which represents the patient in the form of a graph, and includes previous healthcare resource utilization, HCRU, information of the patient as a patient HCRU subgraph;

receiving an HCRU knowledge graph, HCRU KG, associating healthcare resources with medical services;

receiving potential diagnosis information from a clinician;

identifying and extracting potential healthcare resources and services in the HCRU KG associated with the potential diagnosis to form an HCRU subgraph associated with the potential diagnosis; and performing graph analysis on the HCRU subgraph associated with the potential diagnosis and the patient HCRU subgraph to obtain an updated patient HCRU subgraph taking the potential diagnosis into account.

According to an embodiment of a third aspect, there is provided a computer program which when executed on a computer carries out a method to identify healthcare resources used by a patient given a potential diagnosis, the method comprising:

receiving a patient clinical object, PCO, which represents the patient in the form of a graph, and includes previous healthcare resource utilization, HCRU, information of the patient as a patient HCRU subgraph;

receiving an, HCRU knowledge graph, HCRU KG, associating healthcare resources with medical services;

receiving potential diagnosis information from a clinician;

identifying and extracting potential healthcare resources and services in the HCRU KG associated with the potential diagnosis to form an HCRU subgraph associated with the potential diagnosis; and performing graph analysis on the HCRU subgraph associated with the potential diagnosis and the patient HCRU subgraph to obtain an updated patient HCRU subgraph taking the potential diagnosis into account.

An apparatus or computer program, according to preferred embodiments, can comprise any combination of the method aspects. Methods or computer programs according to further embodiments can be described as computer-implemented in that they require processing and memory capability.

The apparatus according to preferred embodiments is described as configured or arranged to, or simply "to" carry out certain functions. This configuration or arrangement could be by use of hardware or middleware or any other suitable system. In preferred embodiments, the configuration or arrangement is by software.

Thus according to one aspect there is provided a program which, when loaded onto at least one computer configures the computer to become the apparatus according to any of the preceding apparatus definitions or any combination thereof.

According to a further aspect there is provided a program which when loaded onto the at least one computer configures the at least one computer to carry out the method steps according to any of the preceding method definitions or any combination thereof.

In general the computer may comprise the elements listed as being configured or arranged to provide the functions defined. For example this computer may include memory, processing, and a network interface.

The embodiments can be implemented in digital electronic circuitry, or in computer hardware, firmware, software, or in combinations of them. The embodiments can be implemented as a computer program or computer program product, i.e., a computer program tangibly embodied in a non-transitory information carrier, e.g., in a machine-readable storage device, or in a propagated signal, for execution by, or to control the operation of, one or more hardware modules.

A computer program can be in the form of a stand-alone program, a computer program portion or more than one computer program and can be written in any form of programming language, including compiled or interpreted languages, and it can be deployed in any form, including as a stand-alone program or as a module, component, subroutine, or other unit suitable for use in a data processing environment. A computer program can be deployed to be executed on one module or on multiple modules at one site or distributed across multiple sites and interconnected by a communication network.

Method steps can be performed by one or more programmable processors executing a computer program to perform functions of the embodiments by operating on input data and generating output. Apparatus of the embodiments can be implemented as programmed hardware or as special purpose logic circuitry, including e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for executing instructions coupled to one or more memory devices for storing instructions and data.

The embodiments are described in terms of particular embodiments. Other embodiments are within the scope of the following claims. For example, the steps can be performed in a different order and still achieve desirable results. Multiple test script versions can be edited and invoked as a unit without using object-oriented programming technology; for example, the elements of a script object can be organized in a structured database or a file system, and the operations described as being performed by the script object can be performed by a test control program.

Elements have been described using the "HCRU KG builder", "HCRU KG customizer", "patient HCRU engine", "impact estimator" etc. The skilled person will appreciate that such functional terms and their equivalents may refer to parts of the system that are spatially separate but combine to serve the function defined. Equally, the same physical parts of the system may provide two or more of the functions defined.

For example, separately defined means may be implemented using the same memory and/or processor as appropriate.

BRIEF DESCRIPTION OF THE DRAWINGS

Preferred features will now be described, purely by way of example, and with references to the accompanying drawings, in which:—

FIG. 4 shows an example of the data presented on a web front end of a standard categorization of healthcare resources and other medical information;

DETAILED DESCRIPTION

Figure 1:
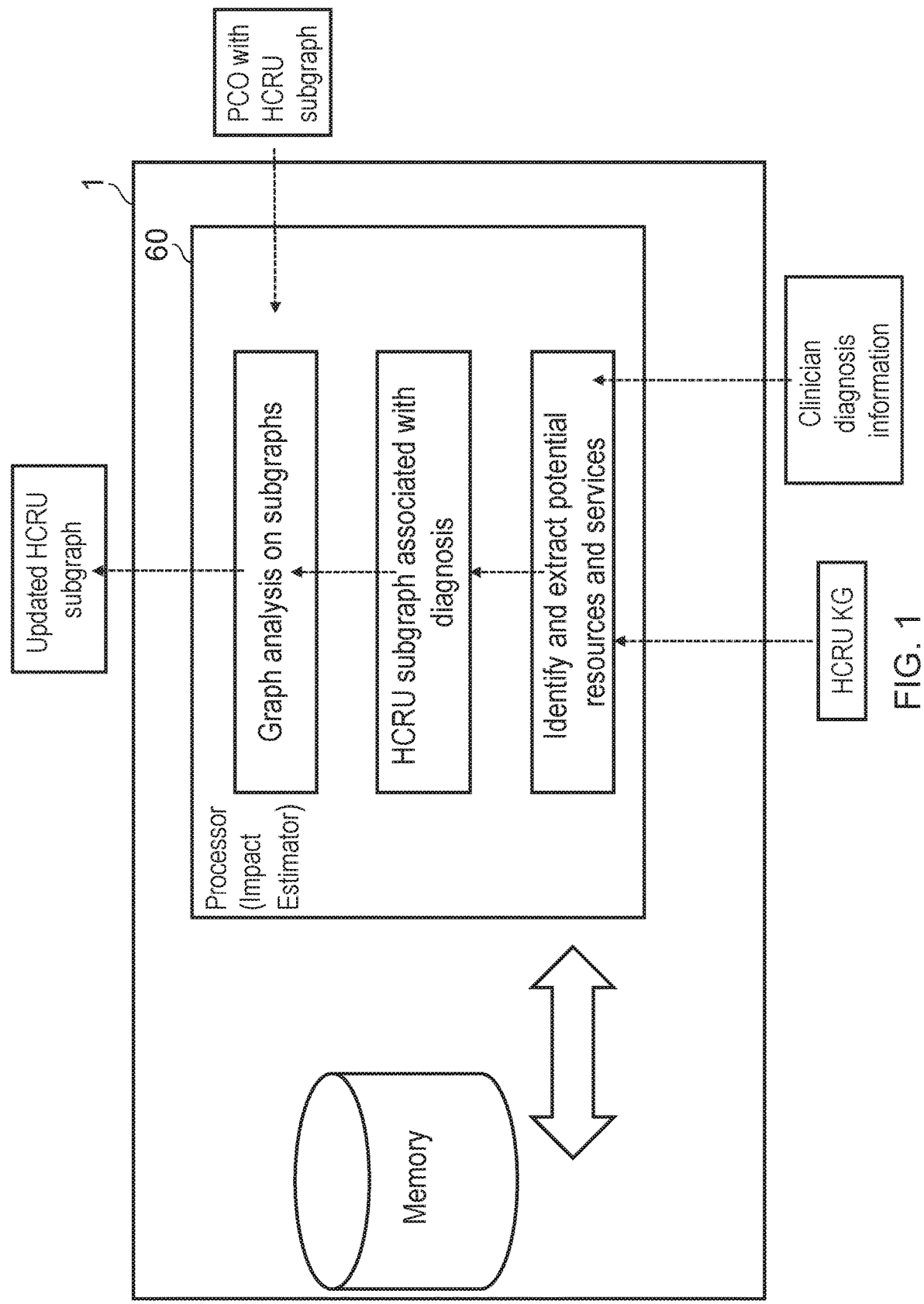
FIG. 1 is a block diagram of main system components in a general embodiment.

Embodiments can provide
- a network of health care resource utilization, represented as a Knowledge Graph, extracted from the literature, public data sources, hospital specific logs and regulations, together with the clinicians' expertise on health care resource utilization;
- a mechanism that identifies the associated health care resource utilization measure for a particular patient given his/her clinical history information, and enrich the patient clinical history with his/her health care resource utilization information;
- a mechanism that estimates the associated resource utilization of a patient when a new diagnosis is detected.

Precision medicine is an emerging approach for disease diagnosis, treatment and prevention that takes into account individual variability in genes, physiology, anatomy, environment, and lifestyle. Precision medicine represents a disruption to the current clinical workflows and resource utilization of the healthcare ecosystem. In this context, embodiments create and use a Knowledge Graph (KG) of health resources utilization along with their specific features, and their associated Patient Clinical Object (PCO) i.e. patient's treatments, diagnosis, and drugs.

This solution establishes and implements a valuable precision medicine within academic medical centers and healthcare clients. Moreover, according to Gartner report on "Hype Cycle for Healthcare Provider Applications, Analytics and Systems", the benefit rating for healthcare resource utilization is high within medical institutions.

BACKGROUND

At the time of writing there is no standard resource for dealing with health resource utilization; there are only ad-hoc resources as plain lists, or matrices for specific areas, for example Health Care Cost and Utilization Report (<URL: www.healthcostinstitute.orq/2014 healthcare cost and utilization report>)

U.S. Department of Health and Human Services (<URL: www.cdc.gov/nchs/data/hus/hus15.pdf>).

Moreover, there are some organizations that are developing resource use measures, for specific regions, and countries Agency for Healthcare Research and Quality (<URL: www.ahrq.gov/>), which includes a chapter of efficiency.

Centres for Medicare & Medicaid Services (<URL: www.cms.gov/>)

National Committee for Quality Assurance (<URL: www.ncqa.orq>)

Quality Alliance Steering Committee (<www.healthqualityalliance.org>)

European Health for All database, World Health Organization, European Region (<URL:www.euro.who.int/en/data-and-evidence/databases/european-health-for-all-database-hfa-db>)

As medical societies, provider organizations, and others look for ways to drive appropriate use of medical resources, hospitals and health systems can play an important role in supporting and guiding these efforts within their organizations. One of the first steps is to identify what is the health care resource utilization among hospital patients. However, efforts to identify this have so far been quite limited.

After having analyzed the related works on health care resources utilization knowledge base the inventors can state that
- there is a lack of methods and tools that exploit the information about healthcare resource utilization and its association to patient clinical data;
- there are no approaches that estimate the potential health care resource utilization of a patient when a new diagnosis is detected.

Embodiments focus effort on the prediction of the healthcare resources utilization to provide a better assistance to the patients without concern about the costs.

The approach uses a deep Healthcare Resource Utilization Knowledge Graph, interlinked, adaptive and scalable to make estimations.

It takes into account a complete PCO (Patient Clinical Object) with all the available information of the patients regarding symptoms, treatments, drugs, etc. in a semantic network structure. Besides, the system receives feedback about historical patients' behaviour in the healthcare resources utilization in past incidents from the PCO, enriching the platform and using this information for future estimations.

Embodiments can achieve accurate and customized estimations for each hospital after analysing Hospital Logs & Regulations using text mining techniques and building Healthcare Resource Utilization subgraphs to calculate the predictions.

General Description

Embodiments create or use a network of health care resource utilization of a given patient. Moreover, the embodiments evaluate the potential impact of a new diagnosis for such patient, in terms of healthcare resource utilization.

FIG. 1 is a block diagram of a system 1 according to a general embodiment for identifying healthcare resources to be used by a patient given a potential diagnosis. It shows a memory which stores instruction for a processor which executes those instructions to form an impact estimator 60. A first identification module in the impact estimator receives input both in the form of a graph of generalized (or medical-institution specific) knowledge about the relationship between services and resources in healthcare (the HCRU KG) and in the form of diagnosis information. This module identifies and extracts potential resources and services associated with a diagnosis. A second module inputs the potential resources and services (which are in the form of a subgraph of the HCRU KG) and inputs the HCRU subgraph from the PCO of a patient. This second module uses graph analysis to provide an updated HCRU subgraph for the patient which takes the potential diagnosis into account.

Figure 2:
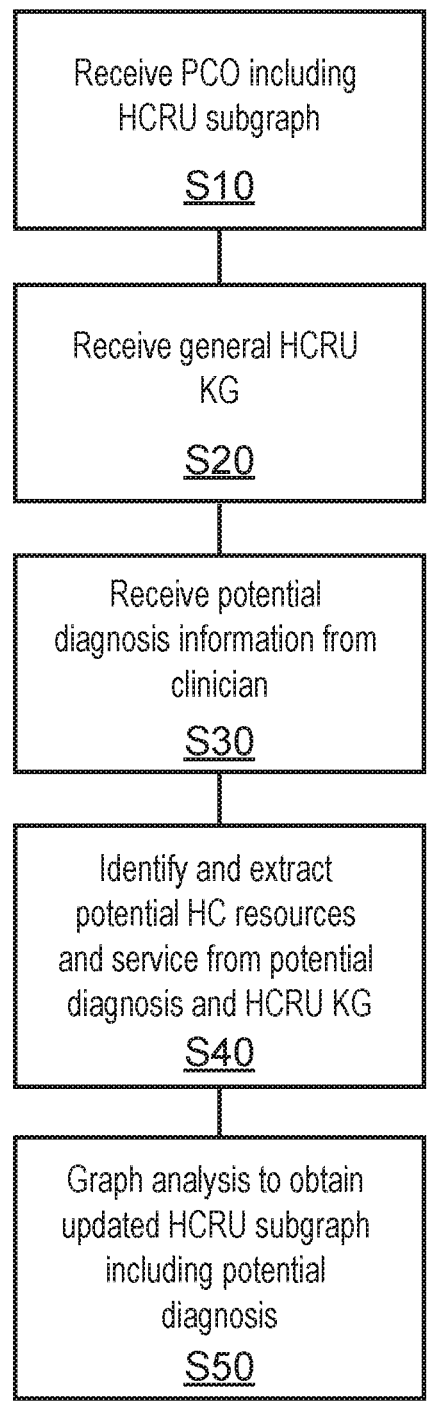
FIG. 2 is a flow chart of a method in a general embodiment.

FIG. 2 shows a flow diagram of a general embodiment providing a computer-implemented method to identify healthcare resources used by a patient given a potential diagnosis. This method includes the following steps:

S10: receiving a patient clinical object, PCO, which represents the patient in the form of a graph, and includes previous healthcare resource utilization information of the patient as a patient HCRU subgraph;

S20: receiving a general healthcare resource utilization, HCRU, knowledge graph, KG associating healthcare resources with medical services;

S30: receiving potential diagnosis information from a clinician;

S40: identifying and extracting potential healthcare resources and services in the HCRU KG associated with the potential diagnosis to form an HCRU subgraph associated with the potential diagnosis; and S50: performing graph analysis on the HCRU subgraph associated with the potential diagnosis and the patient HCRU subgraph to obtain an updated patient HCRU subgraph taking the potential diagnosis into account.

It should be noted that the PCO need not be received until the HCRU subgraph associated with the potential diagnosis is created, because the patient HCRU subgraph is only then required for update.

Detailed Description of a Particular Embodiment

In this embodiment, the system consists of three main core modules and the HCRU KG and patient HCRU KG are created within the system. In other embodiments, they may be provided from other systems. The three core modules are:
- a module for the creation and maintenance of Health Care Resource Utilization Knowledge Graph (HCRU KG), based on information extracted from the literature and public data sources together with the clinicians' expertise on that matter; and
- a module that associates and annotates the patient clinical history with the HCRU, creating in this way a Patient HCRU sub-graph; and
- a module that estimates the impact of a potential new diagnosis in the patient, in terms of health care resource utilization.

Figure 3:
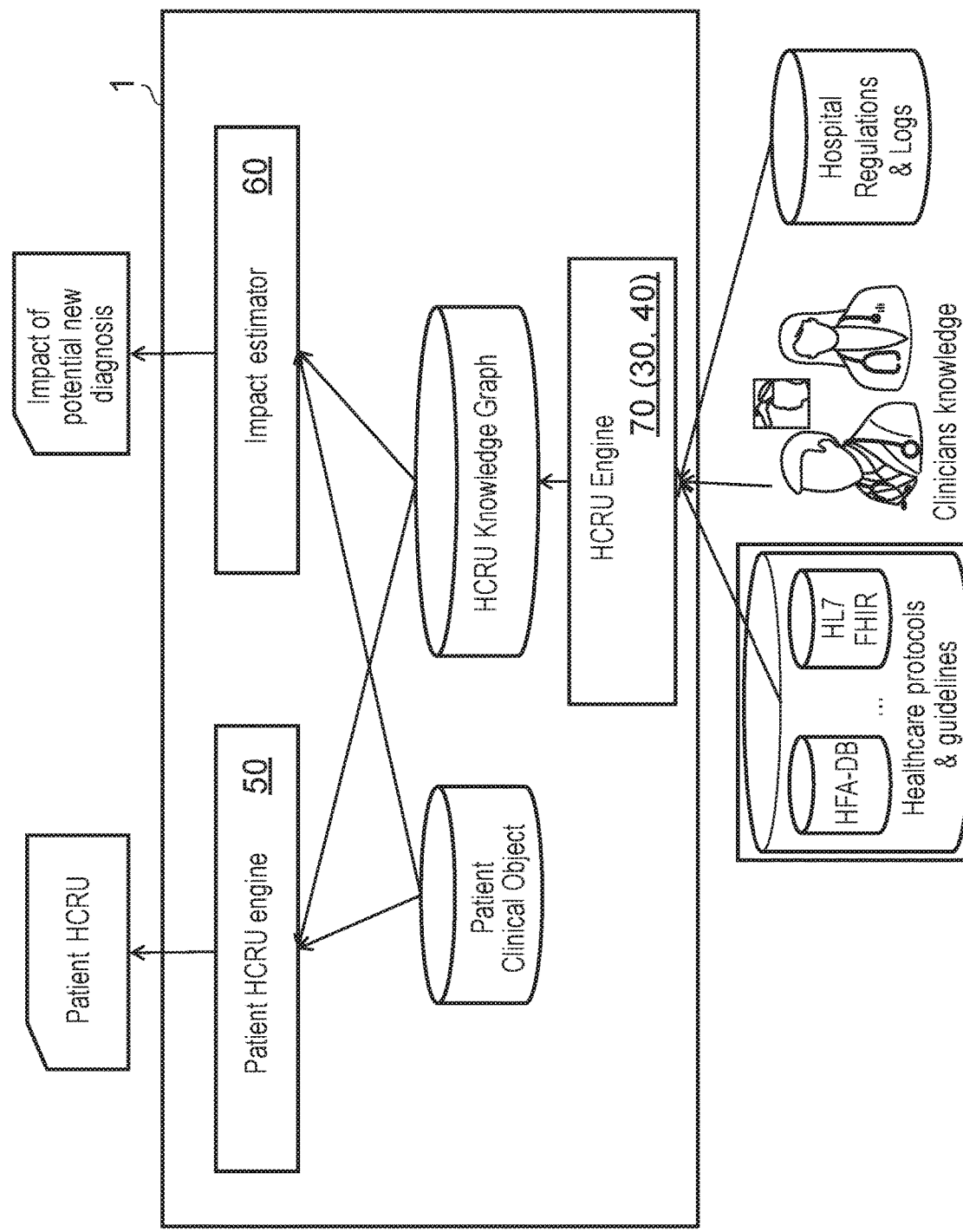
FIG. 3 is a diagram of a specific embodiment.

As shown in FIG. 3, one embodiment of the system includes a Health Care Resource Utilization (HCRU) Knowledge Graph (KG) Engine module 70, which uses open data such as information obtained from the relevant online literature, and available standards. This HCRU KG engine encompasses the healthcare resource utilization, HCRU, knowledge graph, KG, builder 30 and the HCRU KG customizer 40. The patient HCRU graph engine module 50, associates/annotates the existing patient clinical history with the HCRU Knowledge Graph. The impact estimator module 60 estimates the impact of a potential new diagnosis on the patient, in terms of health care resource utilization graph.

It is worth mentioning that the embodiments rely on the "Patient Clinical Object" that is defined as a semantically rich aggregation of clinical entities that encapsulates information about a given patient. This PCO contains information about the patient and its clinical data, including diagnoses, drugs, symptoms and services used.

PCO

The PCO may be provided by a PCO builder (not shown). This PCO builder module can be part of the system, or provided by a separate system. It takes as input the following information:

- Expert knowledge provided by doctor/clinicians in the form of rules coded in a computer language. The clinicians input the rules as text plain files. Basically, the file consists of several rows, and each row contains 2 diagnoses and the relation between them. For example:
  Diagnosis1,relationA,Diagnosis2
  Diagnosis3,relationB,Diagnosis4
  Examples of rules are incompatible diagnoses, and prevalence of diagnosis
  290.0, prevailing over, 290.4
  300.0, incompatible with, 309
  Where 290.0 corresponds to Senile dementia, uncomplicated, and 290.4 corresponds to Vascular dementia. Also, 300.0 corresponds to Anxiety states, and 309 corresponds to Adjustment reaction.
- Previous diagnoses provided by other clinicians as they are recorded in the patient clinical history. These diagnoses will be based on existing international standards such as ICD9 and ICD10 (the ninth and tenth revisions of the International Classification of Diseases).
- Data related to the patient's visits to the hospital and the associated points of care, including the frequency, timeframe, and any resources the patient has used, if this resource information has been included on an ad hoc basis in the patient's notes.
- Biomedical research literature, extracted from literature repositories such as PUBMED, related to diagnoses, diseases, treatments, etc (PUBMED is a service of the US National Library of Medicine (NLM) and provides free access to the NLM database of nursing, veterinary, healthcare, medical and scientific articles).
- Prescription and dispensing of drugs, and their adverse drug reaction, based on European and international standards, such as ATC (Anatomical Therapeutic Chemical Classification).
- A set of knowledge extracted from available medical standards such as SNOMED CT (a standardised, multilingual vocabulary of terms relating to the care of the individual).

The open data (in the last 3 bullet points above relating to the Biomedical research literature, prescription and dispensing of drugs and set of knowledge from available medical standards) is used for enrichment of the terms. That is, the PCO may be enriched by equating PCO parts with standard vocabulary from the classifications listed above and hence annotating entities in the patient data as necessary with corresponding concepts/information from the open data. This facilitates later use of the PCO in conjunction with other standard data.

The expert knowledge need not be essential to make the PCO, but can be used to verify and potentially enrich the knowledge in the PCO, for example by adjusting the diagnoses in the PCO using the expert knowledge, to make sure they are in line with current medical thinking. Additionally or alternatively, any diagnoses in the PCO which are in contradiction with the expert knowledge may be highlighted to the user for manual input and in this way the expert knowledge can act as a cross-check for the quality of the PCOs.

The patient clinical object builder collects, extracts, integrates, curates and cleans the aforementioned data sources and produces the Patient Clinical Object (also known as a patient's egocentric network or ego-net) for each patient, which contains all the related information about the patient, namely age group, gender, a list of hospital visits grouped by unit, e.g., emergency room, outpatient, inpatient, and day hospital, and a list of previous diagnoses grouped by hospital visits and units.

The PCO can be produced from clinical data as a graph centered on the patient vertex, with information about the patient at neighboring vertices linked along edges to the patient by categories, such as any of diagnosis, symptom, treatment, hospital visit and prescription. The clinical data may be provided, for example from hospital records, or health authority records.

HCRU Engine 70

Figure 4:
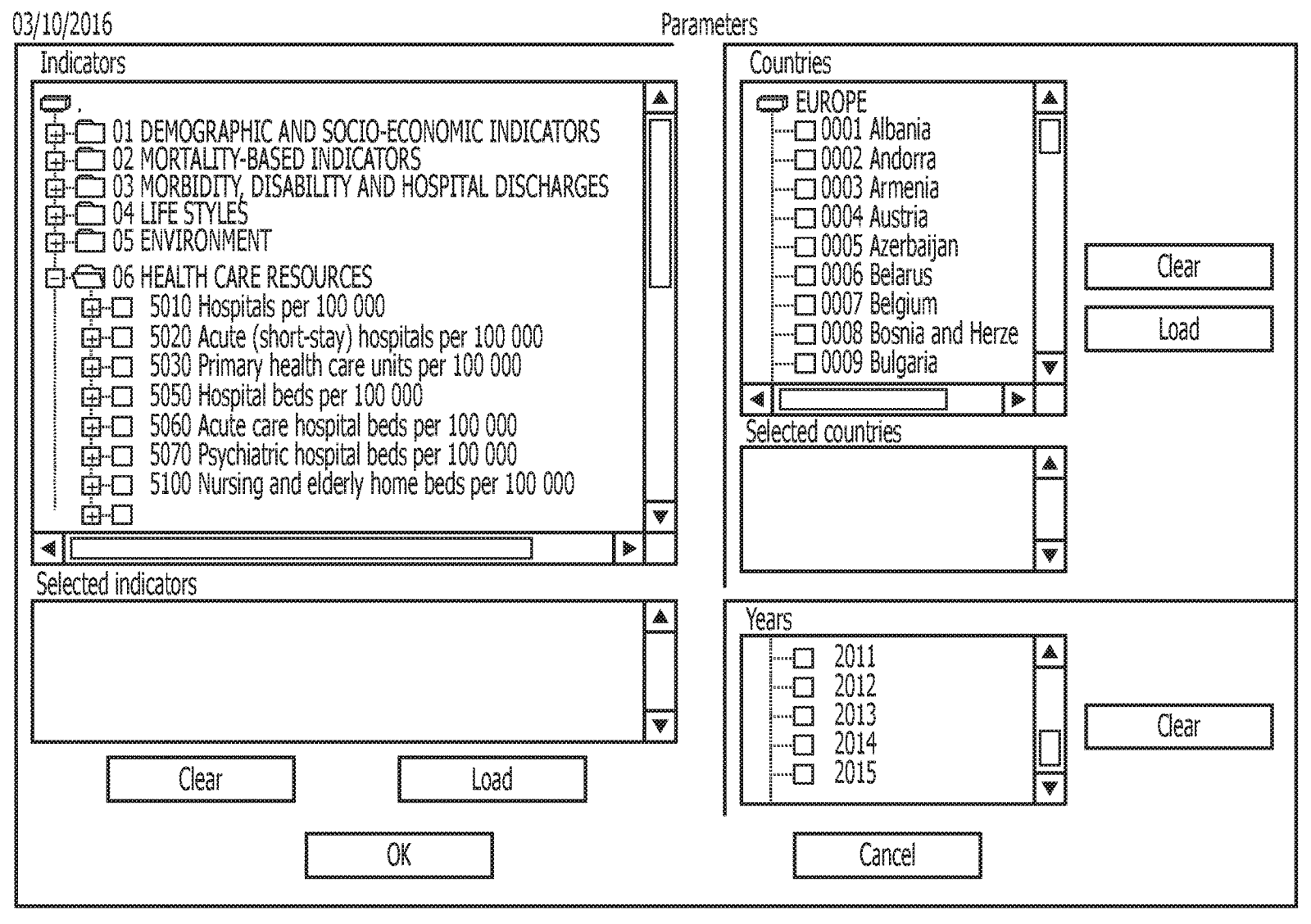

This module captures the evidence based on data derived from literature and public data sources, such HFA-DB, European health for all database, health care resources and health care utilization and expenditure (http://data.euro.who.int/hfadb/) and HL7-FHIR, Fast Healthcare Interoperability Resources (https://www.hl7.org/fhir/summary.html). In a nutshell, the aforementioned public data sources organize the healthcare resources and services and provide a web front end for querying the information. The underlying data is stored in a data storage volume. FIG. 4 shows an example of the data presented on the web front end, for HFA-DB.

There are also other plain lists of healthcare services, in some cases only for a particular country or region, e.g., http://www.wpc-edi.com/reference/codelists/healthcare/health-care-service-type-codes/]

This HCRU Engine module includes two main sub-modules, an HCRU KG builder 30 and an HCRU KG customizer 40, which each in turn consist of several components.

HCRU KG Builder (or HCRU Engine) 30

Figure 5:
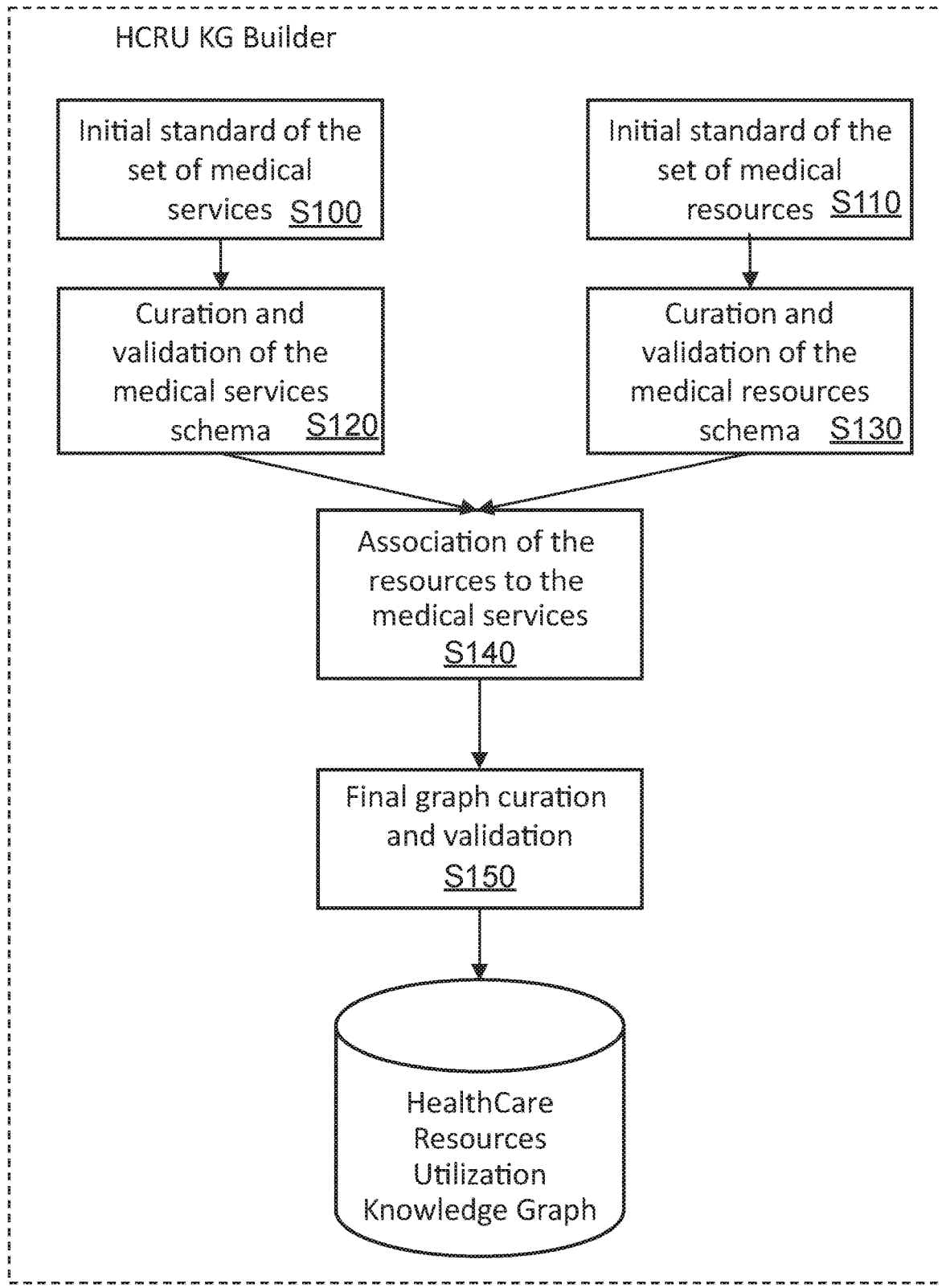
FIG. 5 depicts the main flow of the HCRU KG builder sub-module.

FIG. 5 depicts the main flow of this sub-module. This sub-module comprises components which:
- collect and generate a set of medical services categories (see S100).
- collect and generate a set of healthcare resource utilization related terms (see S110).
- reconcile the medical services and healthcare resource utilization related terms to information extracted from the literature and public data sources, such as the database from World Health Organization (<URL: www.euro.who.int/en/data-and-evidence/databases/european-health-for-all-database-hfa-db>),
- generate initial knowledge models from the set of medical services and resource utilization related definitions and links to literature and public data concepts.
- validate and curate the initial knowledge graphs, potentially with the help of clinicians' expertise (S120, S130).
- perform association between the medial services network with the medical resources utilization parameters (S140).
- curate, and refine the resultant entities and relations with the support of the clinicians (S150).

Figure 6:
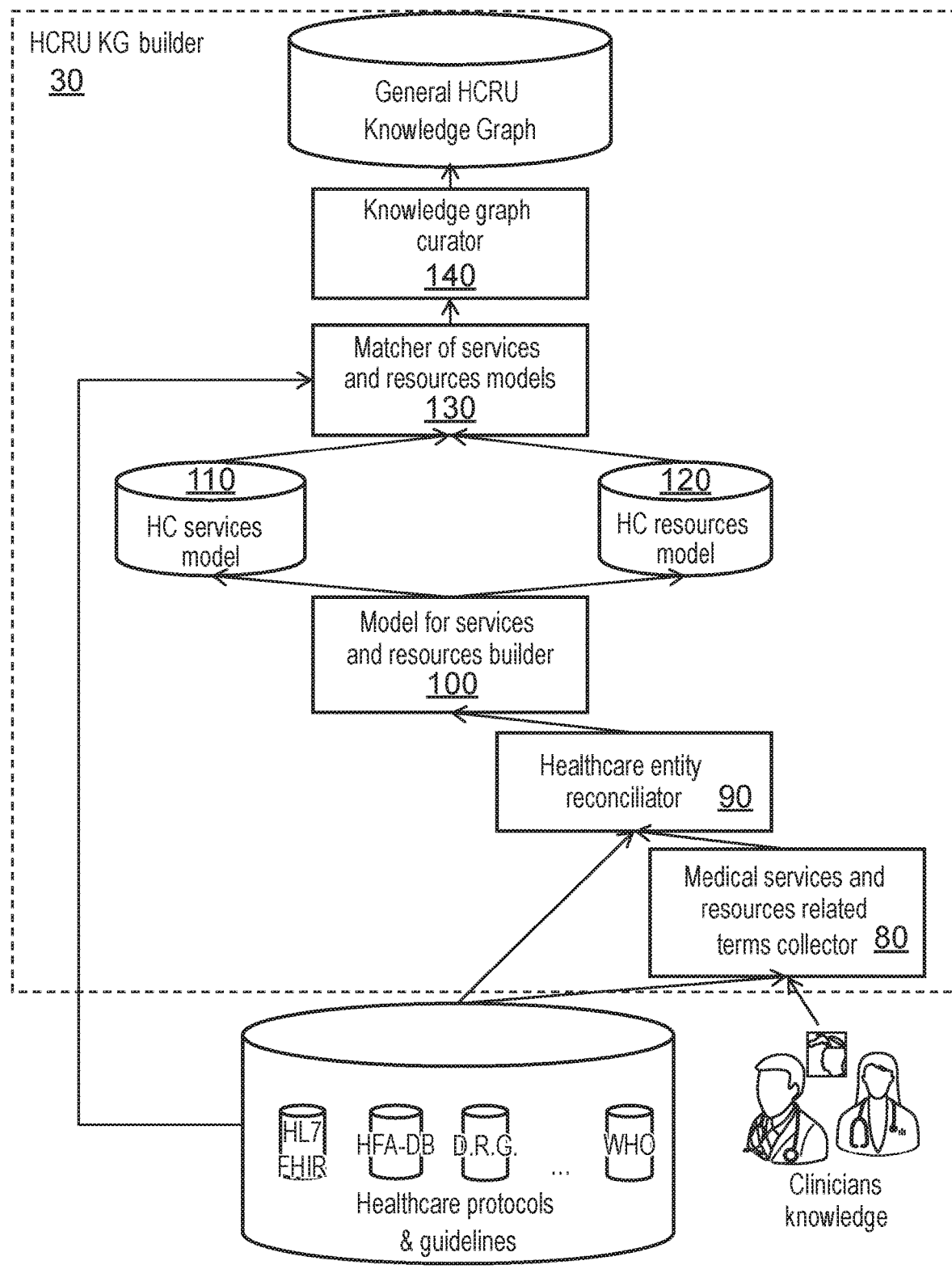
FIG. 6 illustrates the main components of the HCRU KG Builder.

FIG. 6 illustrates the main components of the HCRU KG Builder 30, as explained in more detail below.

Medical Services and Resources Related Terms Collector 80

Figure 7:
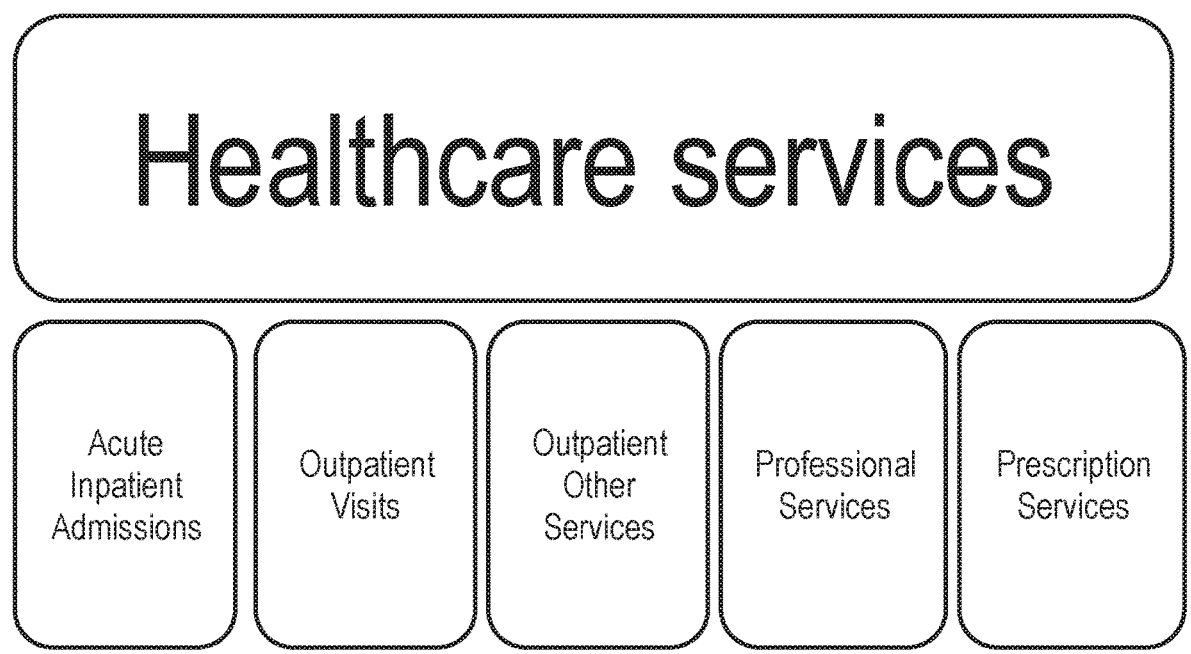
FIG. 7 is a conceptual diagram of top level concepts of an HC service hierarchy model.
Figure 8:
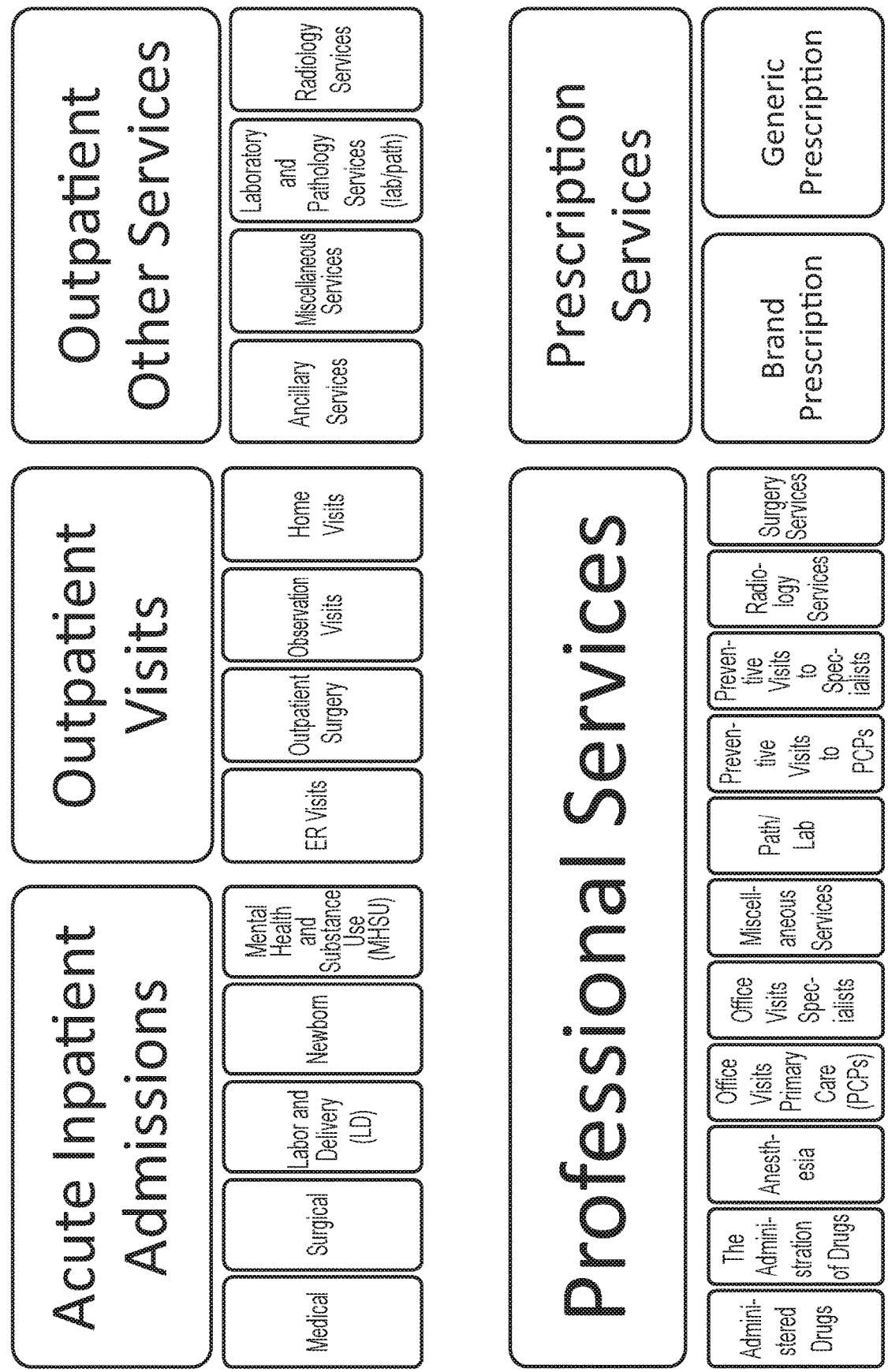
FIG. 8 is a conceptual diagram of subgroup concepts in the HC service hierarchy model.

This component is in charge of interacting with the clinicians who input the seed of resources utilization related terms into the system. According to the clinicians the terms will be grouped in five main groups. These top level concepts of the HC services model are (as shown in FIG. 7):
- Acute Inpatient Admissions
- Outpatient Visits
- Outpatient Other Services
- Professional Services
- Prescription Services These concepts are to be grouped in the following sub-groups (as shown in FIG. 8)
- Acute Inpatient Admissions
  - Medical
  - Surgical
  - Labor and Delivery (LD)
  - Newborn
  - Mental Health and Substance Use (MHSU)
- Outpatient Visits
  - Emergency Visits (ER Visits)
  - Outpatient Surgery
  - Observation Visits
  - Home Visits
- Outpatient Other Services
  - Auxiliary Services
  - Miscellaneous Services
  - Laboratory and Pathology Services (Lab/path)
  - Radiology Services
- Professional Services
  - Administered Drugs
  - The Administration of Drugs
  - Anaesthesia
  - Office Visits Primary Care (PCPs)
  - Office Visits Specialists
  - Miscellaneous Services
  - Path/Lab
  - Preventive Visits to PCPs
  - Preventive Visits to Specialists
  - Radiology Services
  - Surgery Services
- Prescription Services
  - Brand Prescription
  - Generic Prescription It is worth mentioning that this can be a tentative and initial set of terms suggested by the clinicians' expertise, it is not an exhaustive or complete, and can be supplemented as necessary. Moreover, it only includes health care services.

Regarding the classification of the resources terms, they do not necessarily have a hierarchy scheme. Since resources are physical items, people, time, etc. the presentation of the resources' collector will be a list of terms or cluster of terms more than a hierarchy itself.

Taking into account this approach, the categorized list of health care resources terms can be extracted from the healthcare literature and the clinicians' expertise. Categories can be, for example, time taken, people resource, administrative people resource and item resource, as exemplified in the excerpt of seed terms below.
- Time resource
  - Time of visit
  - Time of surgery
  - Time of journey to home visits
  - Time of delay/wait
  - People resource
- Clinicians
  - Number of doctors
  - Number of nurses
- Administrative/management people
  - Number of receptionists
  - Number of consultants
  - Number of porters
- Number of other people involved
- Item resource
  - Beds
  - Ambulance
  - Number of prescriptions (related to Drug Prescription in PCO)

Number of operation rooms
Number of post-operation rooms
Number of recovery rooms
Number of waiting rooms
Number of surgical items required
Number of tests
Number of visits/observations
Breakfast/Lunch/Dinner Finally, the component will collect and store the enhanced sets of terms into the system.

Healthcare Entity Reconciliation 90

This component aims at identifying multiple representation of the same real-word object, in other words identifying equivalent terms in the two different data sources. In this particular case this may be by performing matching/alignment between the collected terms from the clinicians and one or more public data sources offering a standardized (and maybe multilingual) vocabulary of terms related to health care services and/or resources. The outcome of the component is to have the enhanced set of terms, proposed by the clinicians, annotated in standardized terms.

Figure 9:
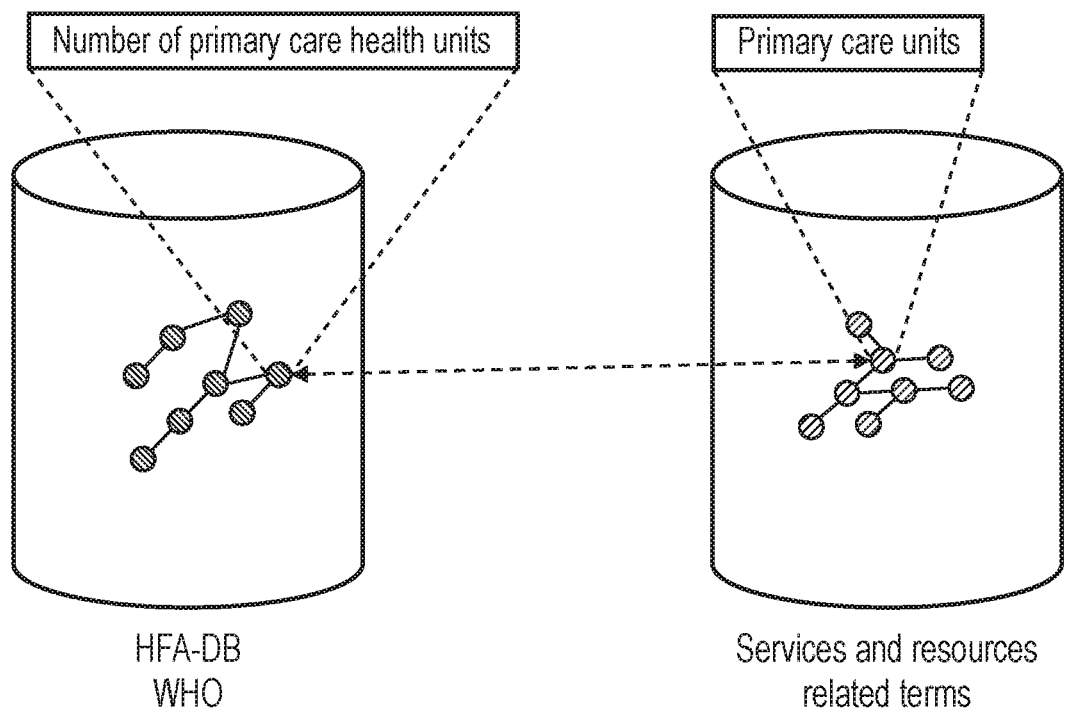
FIG. 9 shows an example of reconciliation between a term in a standard database and a similar term from clinician input.

FIG. 9 shows an overview example of reconciliation between the HFA-DB term "Number of primary care health units" from WHO and the services and resources related term "primary care unit" from clinician input.

Model for Services and Resources Builder 100

Figure 10:
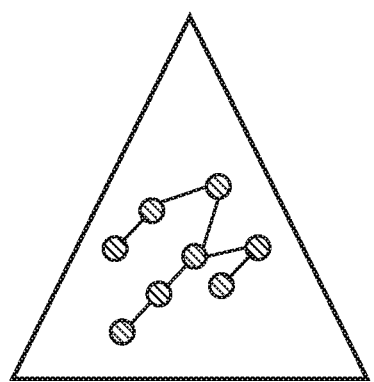
FIG. 10 is an overview of the output of the model builder.
Figure 10:
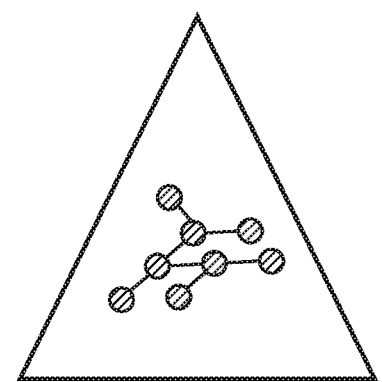
Figure 11:
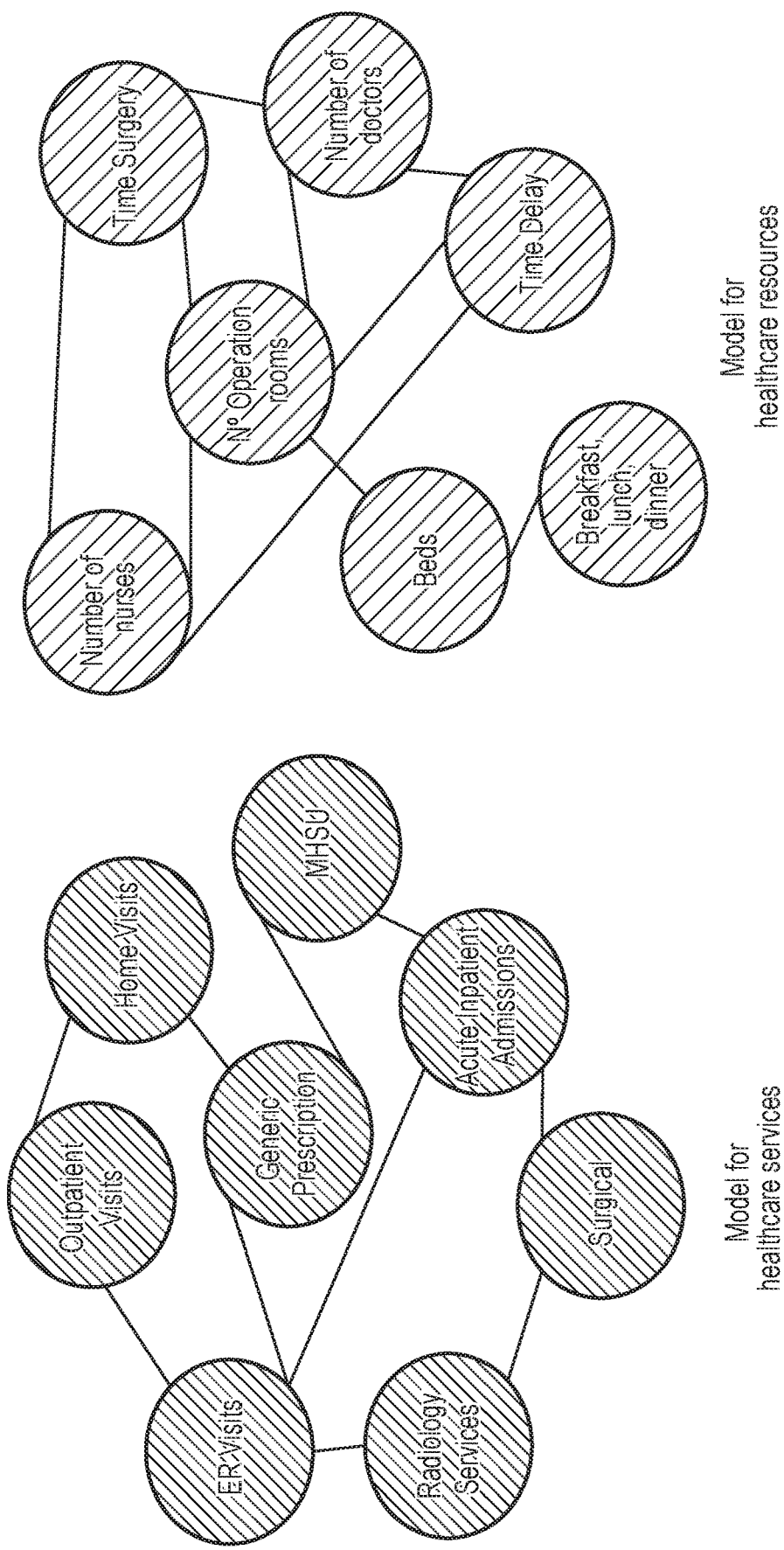
FIG. 11 illustrates exemplary vertices of both models and their internal connections.

This component takes as input the set of terms and their relations and creates an initial set of two models, 110 and 120, one for representing the information of healthcare services and other for representing healthcare resources. FIGS. 10 and 11 present the output of this component.

FIG. 10 is an overview of the output of the model builder, showing the two separate models. FIG. 11 illustrates exemplary vertices of both models and their internal connections, which are formed according to the structure of the clinician information and of the open health data used.

Matcher of Services and Resources Models 130

Once we have the two models representing healthcare services and resources, it is time to create relations between those services and resources. This component is in charge of creating links that relates healthcare services with the resources.

Basically, the component extracts the relations, by performing a relation mining analysis, of the previously identified entities from the public data sources, which are part of the models for healthcare services and resources. The extracted relations will also have a score based on the number of occurrences of the relations within the open data standards/public data sources. For example, the score may be derived from the number of co-occurrences of the terms divided by the sum of the occurrences of either term, or some other suitable metric.

The relations may be labeled with their significance, for example a service may have a particular resource, or a service may imply the presence of a resource and vice versa.

Figure 12:
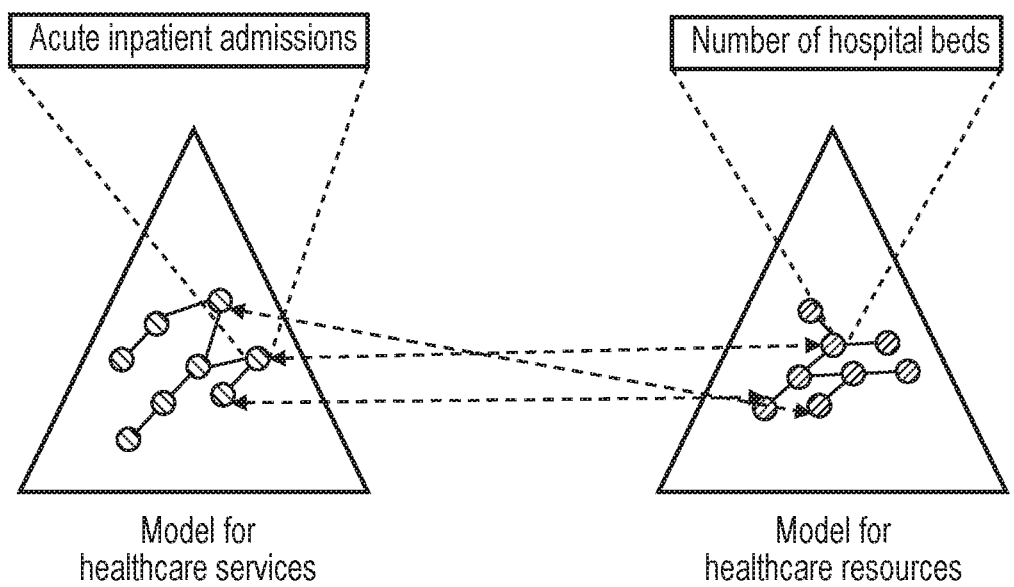
FIG. 12 presents a basic example of the output of the matcher.

FIG. 12 presents a basic example of the output of the matcher, showing a link between acute inpatient admissions and number of hospital beds.

Figure 13:
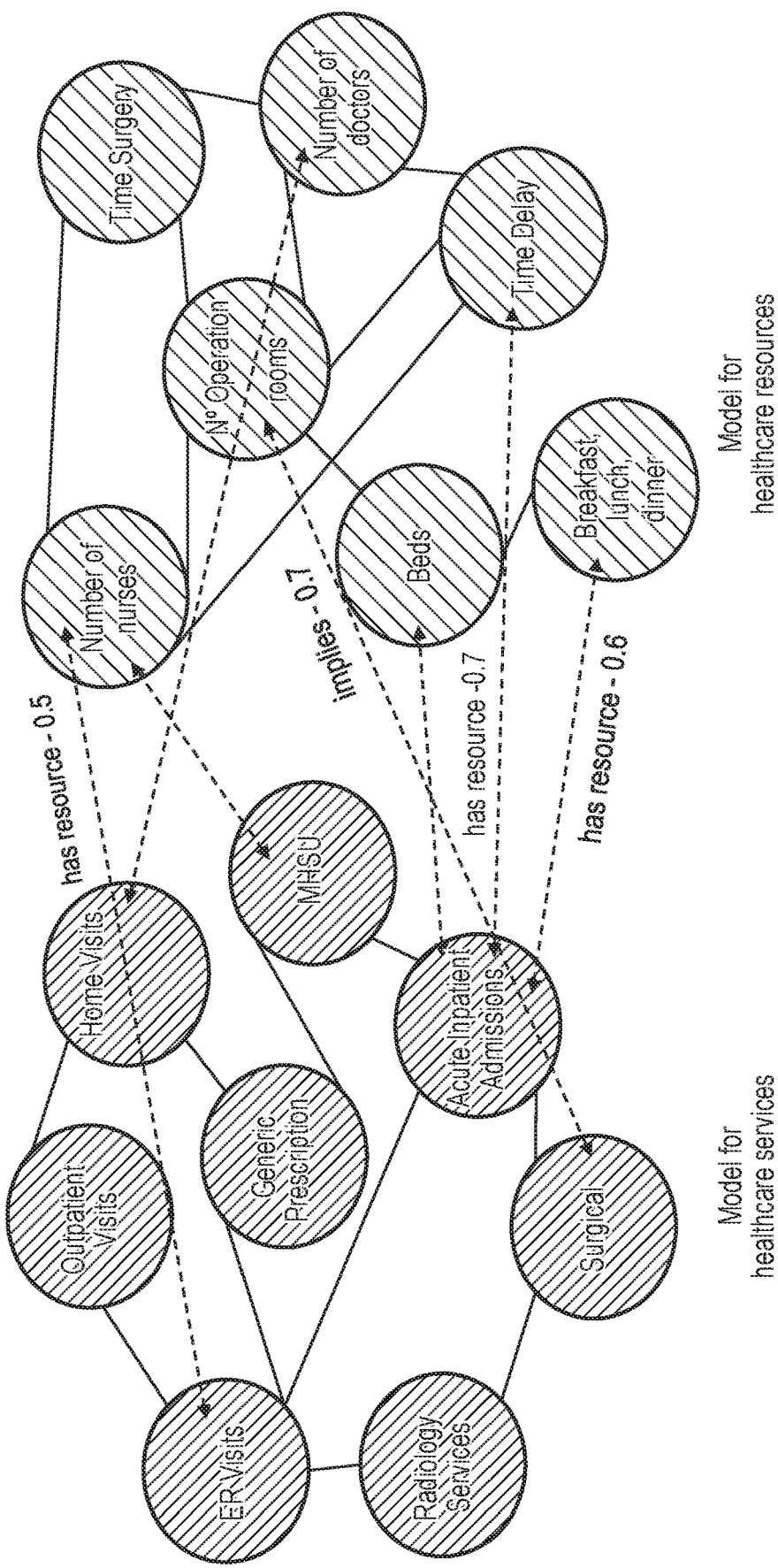
FIG. 13 is a more contextualized example of the output for the matcher.

FIG. 13 is a more contextualized example of the output for the matcher of services and resources models, showing the scores for some exemplary relations.

Knowledge Graph Curator 140

The final module aims at integrating the extracted entities along with their relations, including the scores information mentioned above and the provenance information.

Figure 14:
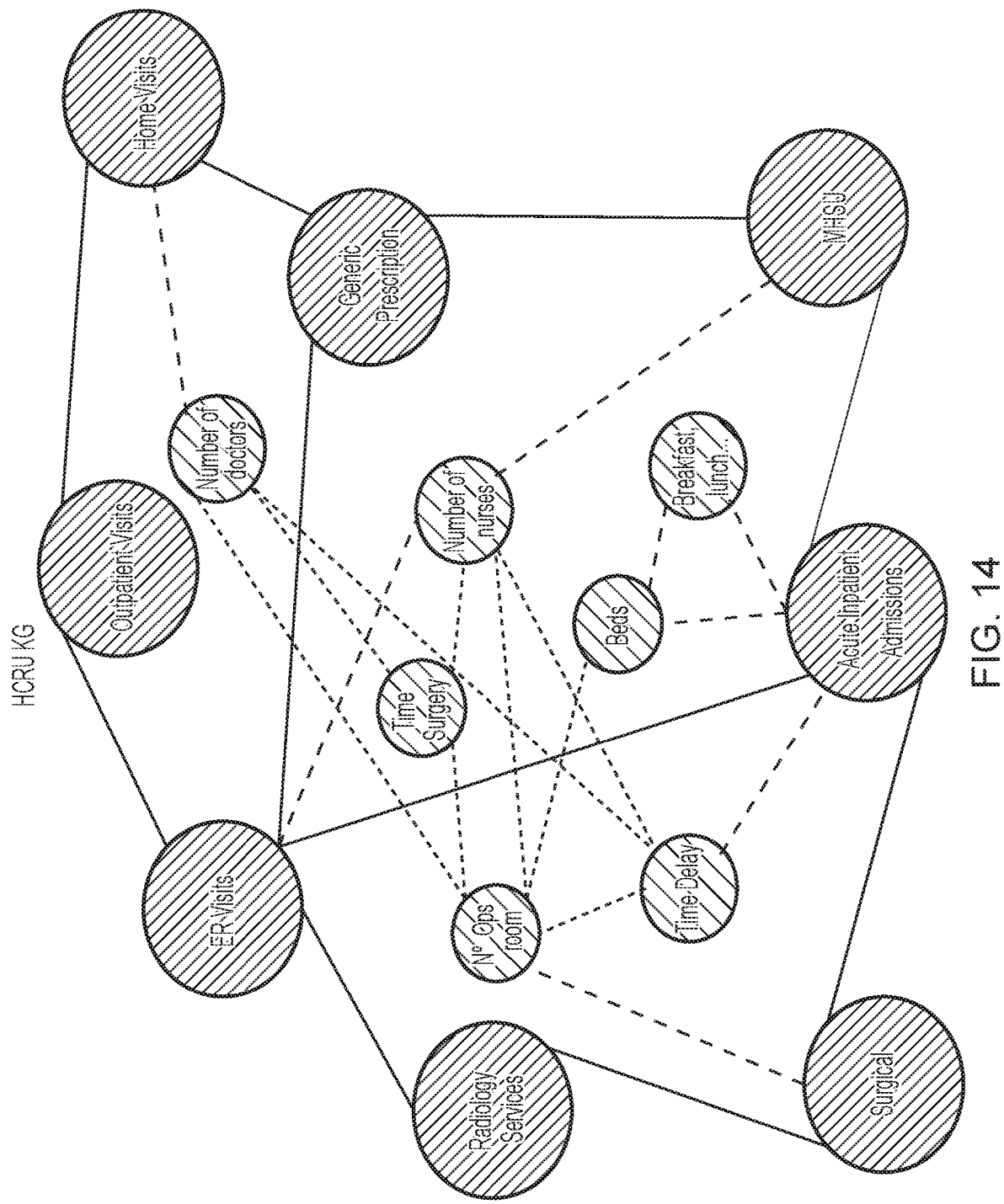
FIG. 14 is a diagram of a knowledge graph in part.

FIG. 14 shows part of an HCRU KG, with the services distinguished from the resources using paler shading.

The system presents the HealthCare Resources Utilization Knowledge Graph to the clinicians in a very intuitive way (in graph form, as shown in FIG. 14), and they will be able to manually curate and fix any potential inconsistencies of the generated graph.

HCRU KG Customizer 40

Figure 15:
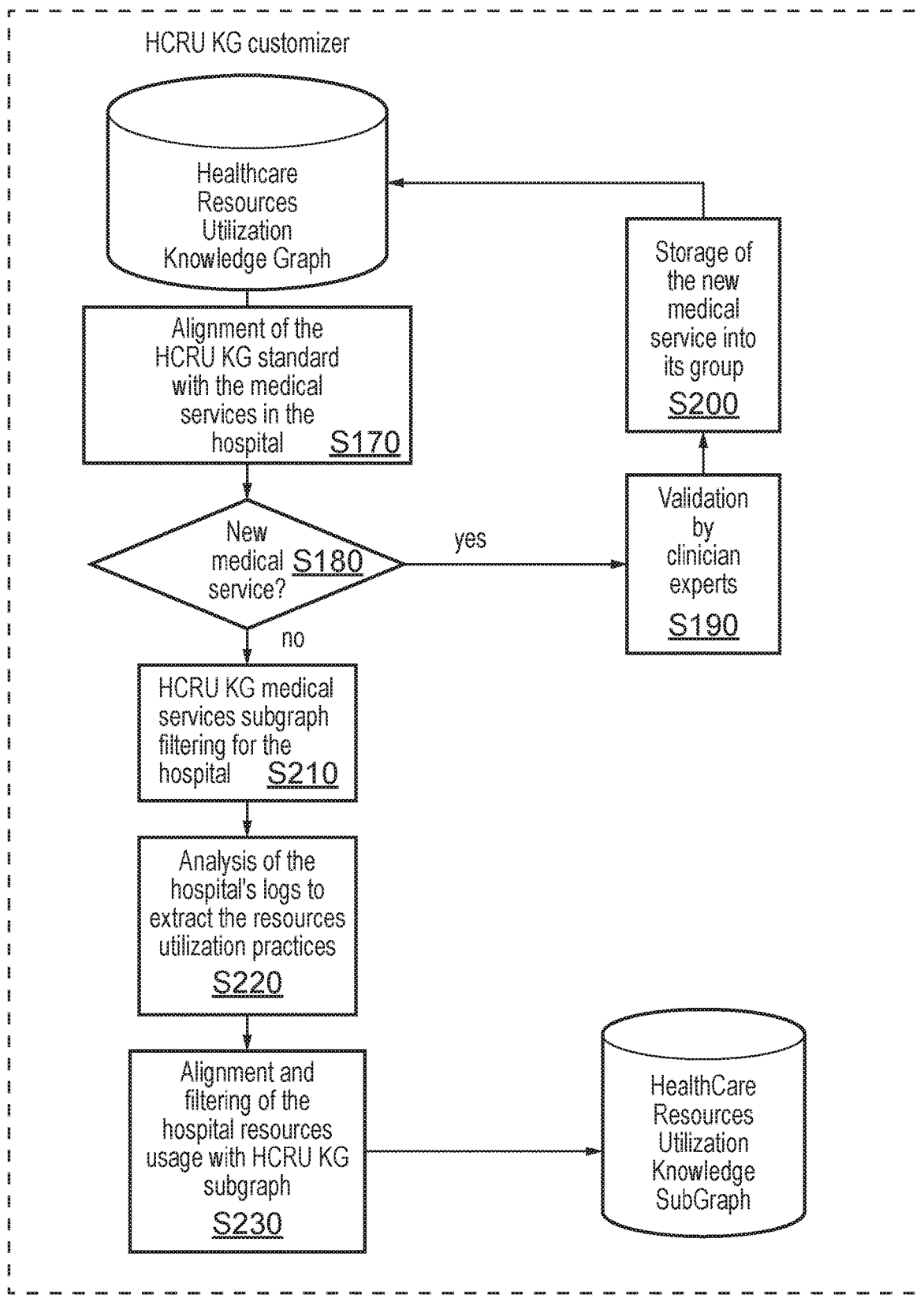
FIG. 15 depicts the main flow of the HCRU KG Customizer 40.

FIG. 15 depicts the main flow of the HCRU KG Customizer 40. This sub-module comprises components which:
align the standard HCRU Knowledge Graph of medical services with the services that are provided within a particular healthcare institution (S170);
check for a new medical service which is not in the HCRU KG (S180), validate the service by clinicians (S190) and store the new medical service in the correct group (S200);
filter and prune the standard to generate a customized subgraph with the medical services of the institution (S210);
perform process mining over available hospital logs and extract behaviour patterns of the resources utilization for a particular medical institution (S220).
filter, generate and customize a subgraph from the previous knowledge subgraph taking into account the resource utilization guidelines of a medical institution (S230).

Figure 16:
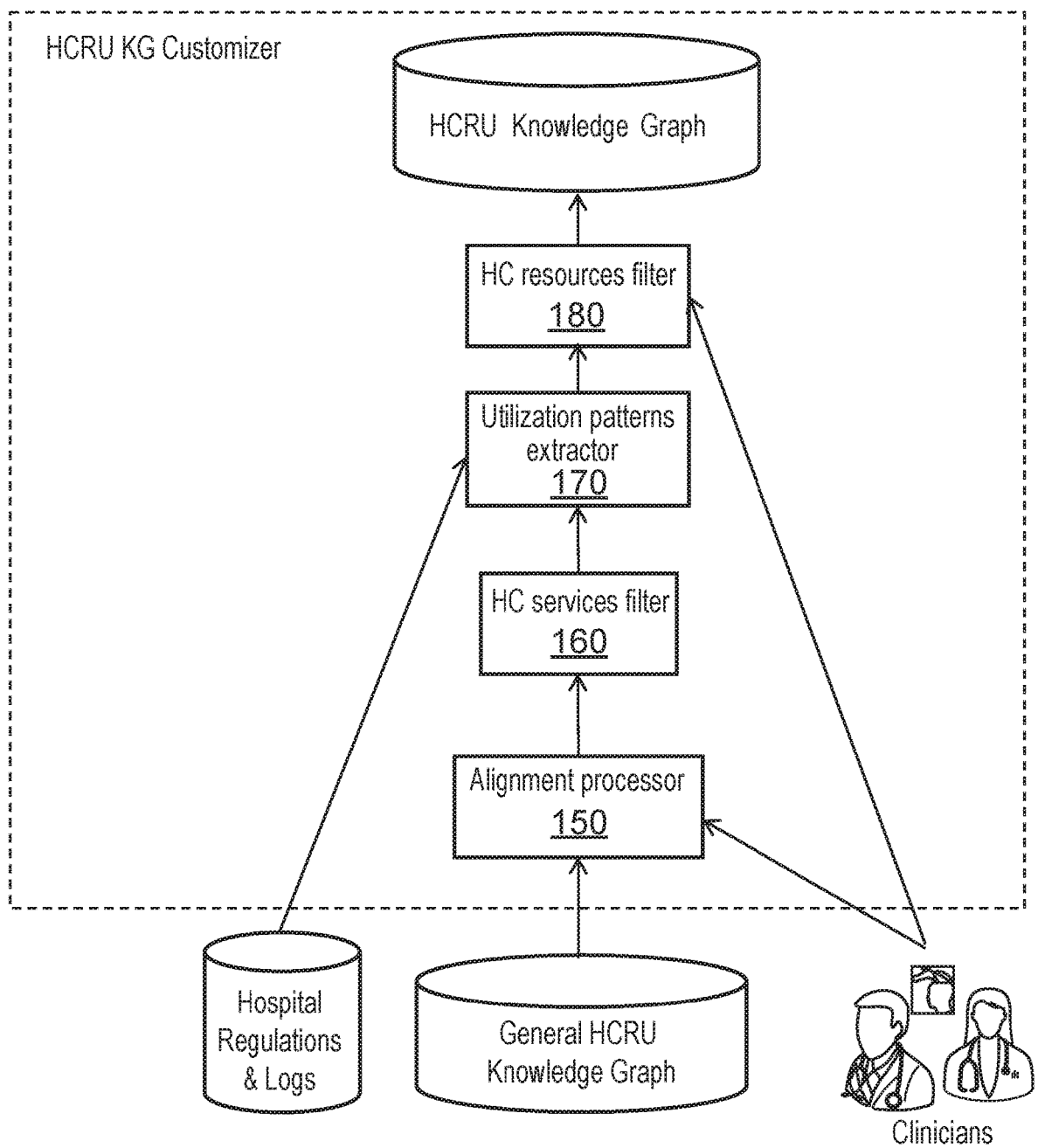
FIG. 16 illustrates the main components of the HCRU KG Customizer.

FIG. 16 illustrates the main components of the HCRU KG Customizer. This sub-module can customize the standard healthcare resources utilization knowledge graph for a particular medical institution. The various components of the customizer are described in the following.

The Alignment processor 150 takes the hospital services portfolio and identifies the services that are contained in the General HCRU KG. Next, the HC services filter 160 removes from the General HCRU KG the services not included in the hospital services portfolio. After that, the Utilization patterns extractor 170, by means of process mining techniques over the Hospital Regulations and Logs, identifies what and how the resources of the hospital are really used. Finally, the HC resources filter 180 removes out all the resources that are not used in the hospital, and it produces the HCRU Knowledge Graph.

One core component of this HCRU KG Customizer is the Utilization patterns extractor 180, which takes the hospital logs, and extracts process knowledge, e.g., process models in order to discover, monitor and improve the healthcare processes specific for the given hospital. A hospital log can be seen as a record of named activities ("Check Medications", "Patient Examination") which is created as a byproduct of EHR use. These events occur in an order relative to each other, usually represented by time stamps. In this context, the component checks if the observed behavior in the logs conforms to the given model, provided by the hospital internal regulations. For example, it may be checked whether a medical guideline which states that always a lab test and an X-ray needs to be done is always followed.

Figure 17:
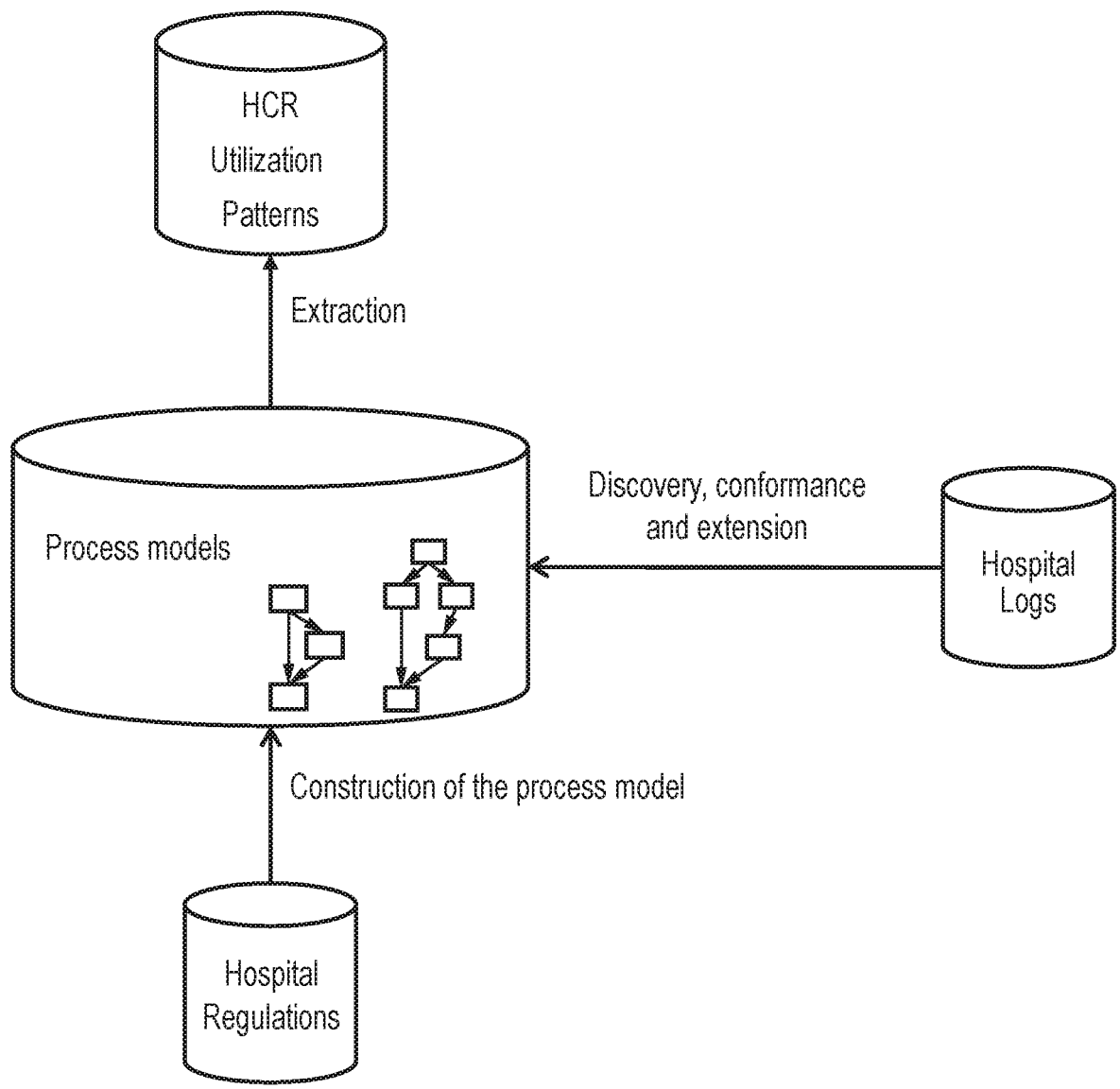
FIG. 17 is a high-level flow diagram of the utilization patterns extractor.

Moreover, the component performs a projection of the information extracted from the logs onto the model, i.e., the hospital internal regulation in this case. For example, performance information may be projected on a discovered healthcare process in order to see for which examinations a long waiting time exists. FIG. 17 shows the flow of this component for this, in which the hospital logs and hospital regulations are matched and patterns extracted to provide HCR utilization patterns.

The HCR utilization pattern contains a customized subgraph of the HCRU KG. This customized subgraph of the HCRU KG will be part of the HCRU KG. As a first approach it is possible to rely on existing, available, and basic approaches for process mining to provide the subgraph.

As previously mentioned, and as seen in FIG. 16, the input of the extractor is the customized version of the HCRU KG for a particular hospital according to the specific services and resources that the given hospital provides. In addition, by checking the logs and internal regulations we can identify how the services and resources are really used by the hospital and modify the subgraph accordingly.

The clinicians and managers will be able to check how the healthcare resources and services are actually used within the hospital. This information will help to enrich the PCO of a particular patient, by including the resources and services the patient is using. In addition this will help with the estimation of the healthcare resource utilization for a potential diagnoses, by use of the impact estimator module.

Patient HCRU Engine 50

Figure 18:
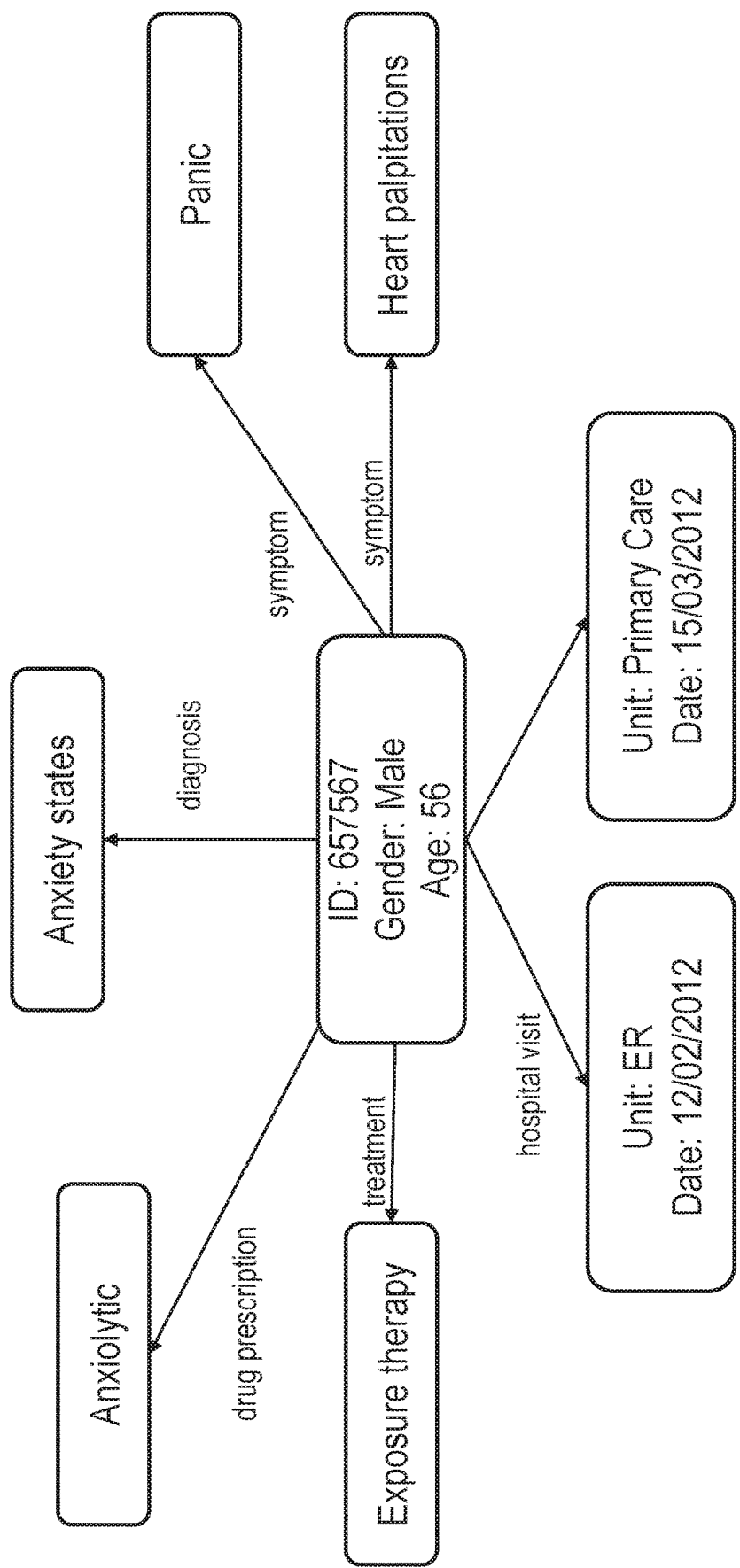
FIG. 18 is an example of a simple PCO.
Figure 19:
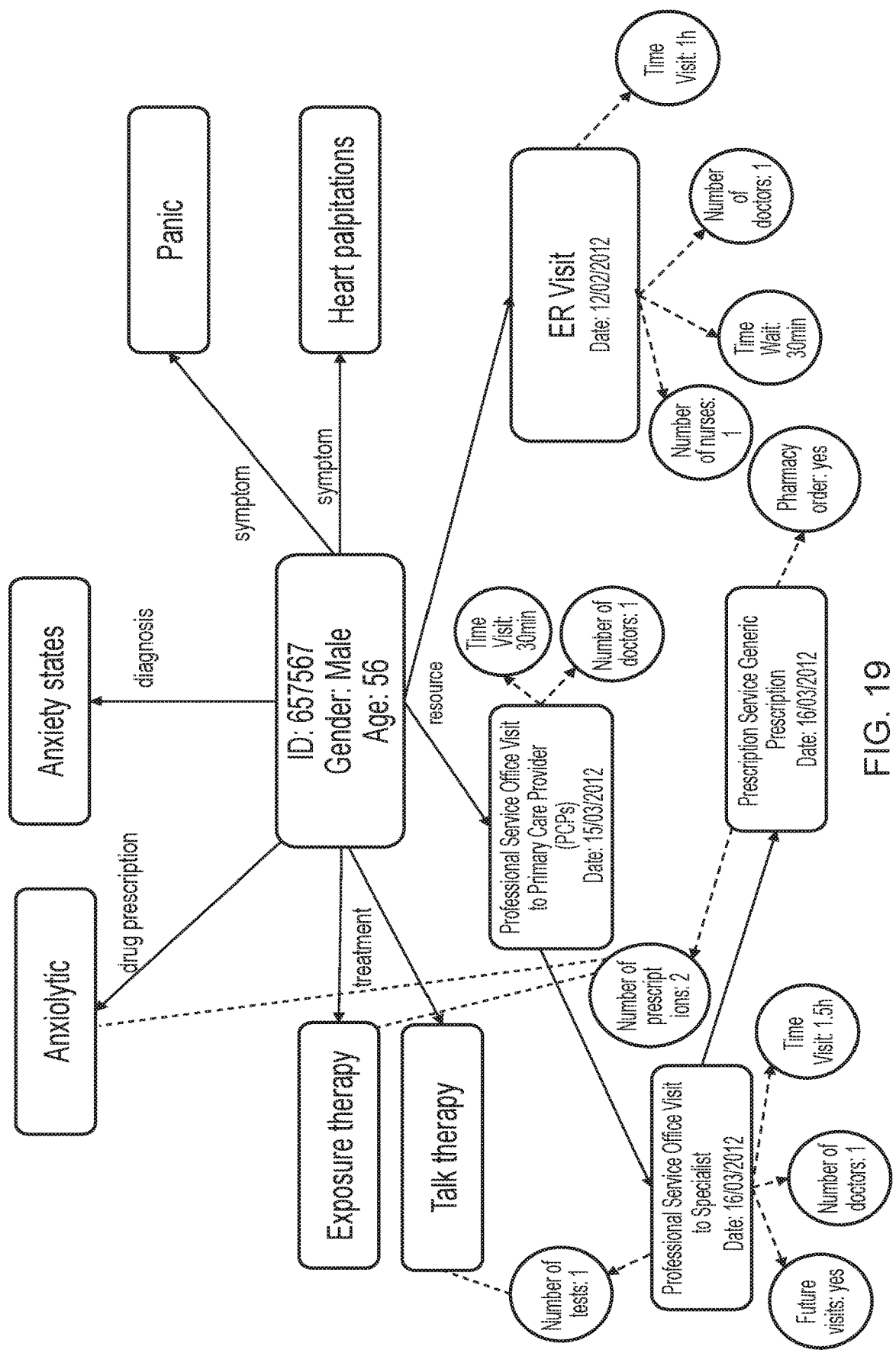
FIG. 19 is an example of a PCO enriched with the HCRU subgraph.

This engine enriches the Patient Clinical Object (PCO) by including information related to the health care resource utilization taken from the HCRU Knowledge Graph. Basically, the module annotates and associates the patient clinical history with concepts from the HCRU. FIG. 18 shows an example of a PCO, and FIG. 19 shows the resultant PCO enriched with the health care resource utilization graph.

The former PCO contains information about clinical history, diagnoses, risks, treatments, symptoms, and drugs. After the enrichment the PCO will include the information about health care resources as exemplified in FIG. 19. In a nutshell, the HCRU KG customized subgraph provides information related to the health care resources, and this information is matched against the clinical history of the PCO, e.g., ER visits or inpatients. Those visits imply that the patient have used some health care resources of the given hospital. Therefore, the enriched (or annotated) PCO reflects this information in FIG. 16.

This enrichment the PCO of a particular patient, by including the resources and services the patient is using will help to identify what resources/services the patient is using and how well or poorly the patient is using the resources/services. Moreover, this will also help to estimate what healthcare resources the patient will use in the future. Finally, the managers will have in a single snapshot what healthcare resources are being used by the patients.

Impact Estimator 60

This module (or stand-alone system) takes as input the annotated PCO that already includes the health care resource utilization (as a subgraph) for the particular patient; potential new diagnosis information for such patient; and the HCRU Knowledge Graph and uses graph mining. The module produces as a result a subgraph of the potential health care resource utilization along with scores. Essentially, nodes of this resultant subgraph, which correspond to the health care resources, each have an individual score that represents the probability of potential use (for that health care resource) for the particular patient when the potential diagnosis is given.

The subgraph of potential health care resource utilization includes nodes from the original HCRU. The graph mining step can be viewed as a "pruning" of the original HCRU graph. This then restricts the subgraph to those resources which are relevant to the potential diagnosis.

The potential diagnosis is related to previous diagnoses, drug prescription, and other health care resources, which are collected together in the system as the PCO. The potential diagnosis data may be manual (for example if it is from the clinician that estimated the potential diagnosis) or semiautomatic (if it is provided with the help of a diagnosis support system).

Figure 20:
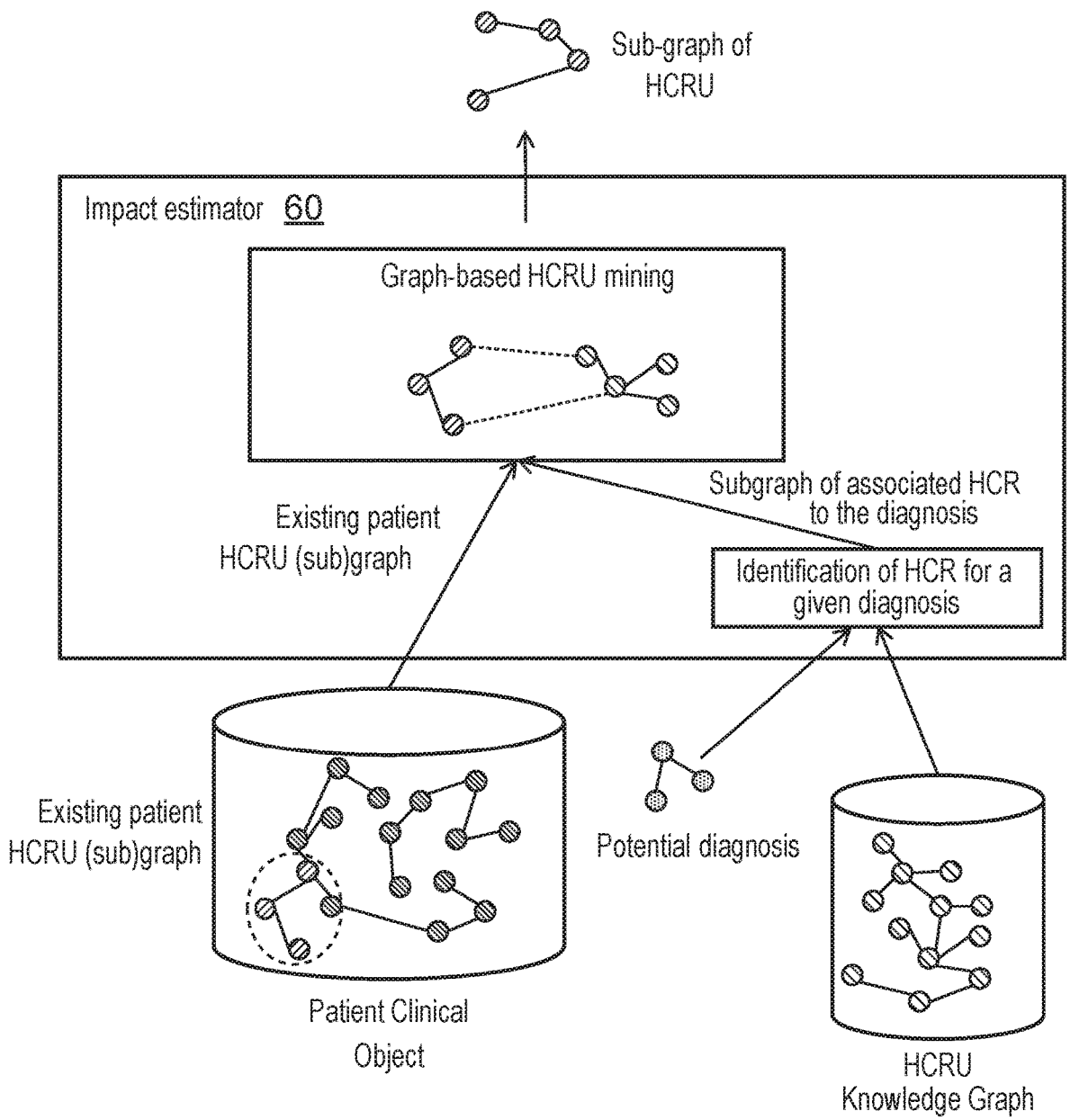
FIG. 20 is a block diagram of an impact estimator.

FIG. 20 shows the impact estimator 60, with inputs from the PCO and the HCRU KG, as well as from a clinician or clinician assisted by a diagnosis support system.

The module takes the diagnosis related information and searches on the HCRU Knowledge Graph using a submodule for the "Identification of HCR for a given diagnosis" that is in charge of identifying for a given diagnosis the related subgraph of the HCRU KG (see FIG. 20).

The HCRU KG includes resources and services, and the diagnosis related information includes a diagnosis and its relations to other symptoms, drugs, and treatments. The relations of drugs and treatments can thus be linked to the HCRU KG.

This search collects potential health care resources and services associated with the new "status" of the patient, after his/her new diagnosis. Once the potential associated health care resources are identified, the impact estimator estimates if these health care resources would affect patient current resource usage and how, using graph-based mining. The outcome is a final HCRU sub-graph for the patient that reflects the potential utilization of resources.

A new diagnosis can affect resource usage in different ways. For example if the diagnosis is that the patient is dead, the hospital will have an empty bed. If there is already a future visit scheduled to a specialist of the same specialty, then potentially more time resource might be required rather than a further visit. In another example, if the diagnosis is that the patient remains on the same status, the doctors might require that he/she stays in a bed and continue to give him/her drugs, or change the drugs or amount thereof. Assuming there is no usage affected by the diagnosis, in that case, if the patient is already in the hospital, the patient would continue using the same resources/services as before.

If a hospital bed is required by the new diagnosis, but a patient is already in a hospital bed, for example, the hospital will have within its records of the patient that he/she is currently hospitalized, so making a match of this information the system knows that the patient does not need an extra bed in that situation. As an aside, specific embodiments of the target health care resource usage estimation for a given patient and diagnosis; but may be integrated with an existing Hospital Information System.

In summary, the graph mining module takes as input the two subgraphs (1) existing patient HCRU sub-graph, and (2) associated HCRU to a given diagnosis; and performs graph analysis to obtain the potential HCRU for the given new diagnosis of the patient. Basically the graph analysis explores all the nodes of the graphs in order to find which nodes (from the different subgraphs) are potentially related and how. Specifically in this case this finds what healthcare resources (and services) from the subgraphs are related and how they are related.

FIG. 20 depicts the flow of the process, including the starting position of the existing patient HCRU subgraph shown at the bottom left, the potential diagnosis at the bottom centre and the HCRU knowledge graph at the bottom right. Combination of the part of the HCRU KG which is relevant to the potential diagnosis (middle right, paler nodes) with the existing patient HCRU subgraph (middle left, darker nodes) forms an interim result and at the top centre is shown the sub graph of the HCRU, following graph mining. Nodes in FIG. 20 are illustrative, they do not represent a particular situation, which is however depicted in the worked example later.

The 3 nodes to the right are shown paler in the graph mining process to highlight that they come from a different places: the HCRU KG at the bottom right (they are not added). The 3 nodes to the left come from the HCRU subgraph of the PCO.

For the "original nodes" coming from the HCRU KG (right bottom part), the related values of the healthcare resources might change, for example to add some time to a specialist visit that is already scheduled.

The dashed lines represent a relation between the nodes coming from the different subgraphs. There are two HCRU subgraphs, obtained from existing modules/subcomponents; and now with these two HCRU subgraphs we perform graph mining to get the resultant final subgraph.

In a nutshell this module has three main tasks:
Identification of HCR for a given diagnosis, in which the module extracts the healthcare resources and services associated to a given diagnosis, for such health care resources in the HCRU Knowledge Graph.
Graph-based resource utilization assessment and mining, in which the module takes as input the two subgraphs (1) existing patient HCRU sub-graph, and (2) associated HCRU to a given diagnosis; and performs graph analysis to obtain the potential HCRU for the given new diagnosis of the patient. Basically the graph analysis explores all the nodes of the graphs in order to find which nodes (from the different graphs) are potentially related and how. Specifically in this case this finds what healthcare resources (and services) from the subgraphs are related and how they are related.

Worked Example

Figure 21:
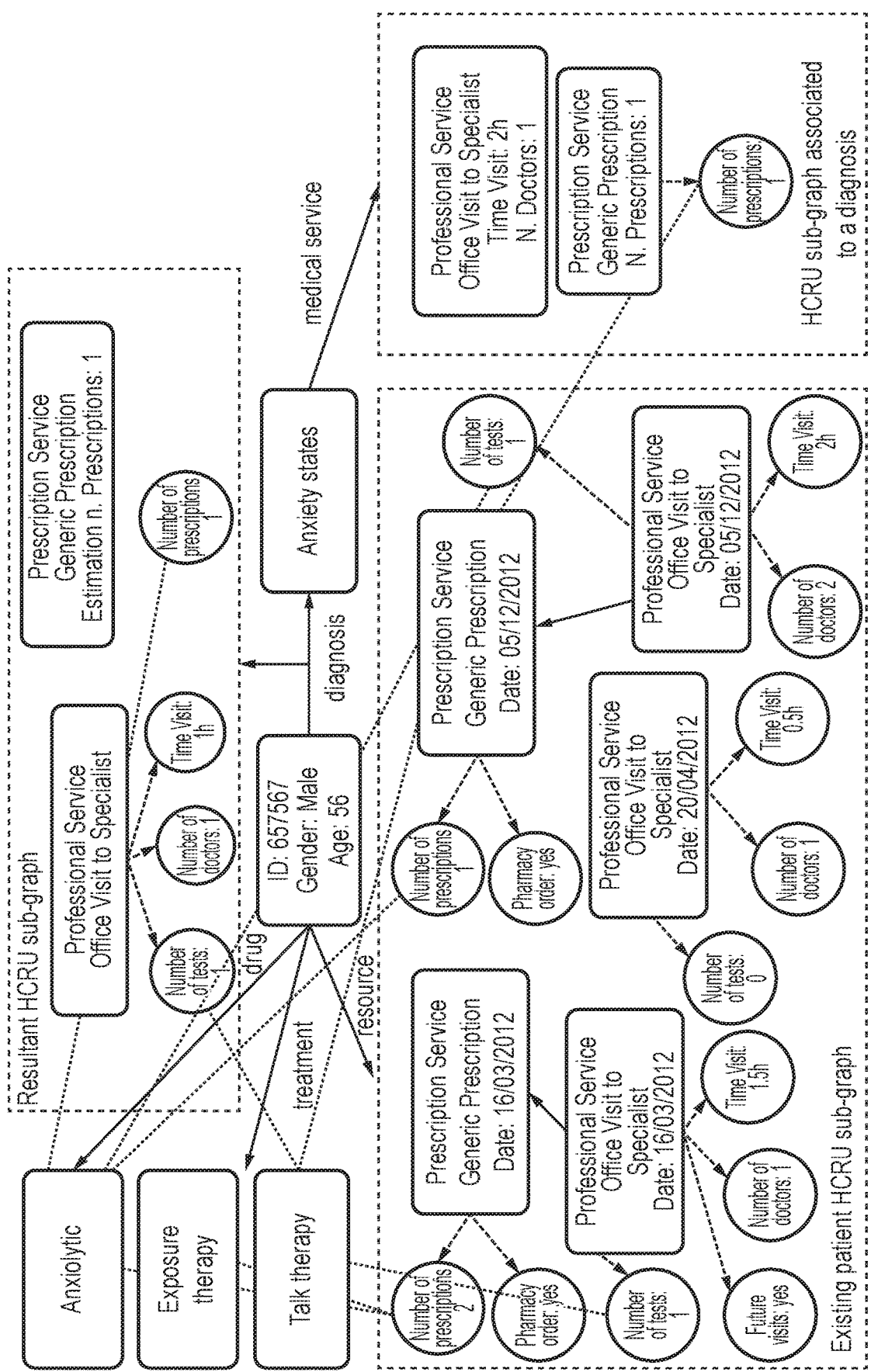
FIG. 21 is a diagram of a patient PCO enriched with an HCRU subgraph corresponding to a potential diagnosis.

FIG. 21 shows a worked example of an existing patient HCRU sub-graph with services and resources, a potential diagnosis of anxiety states and the HCRU sub-graph associated with that diagnosis. The resultant HCRU sub-graph, of which only the additional nodes are shown, includes two additional services and associated additional resources beyond the previous existing patient HCRU subgraph. There is a new prescription (without date, whereas the previous prescriptions are dated in the past) and a new visit to a specialist which uses resources including tests, doctors and a visit of 1 hour. In this particular case, there is no alteration/deletion to the existing patient HCRU subgraph, but simply additions.

Figure 22:
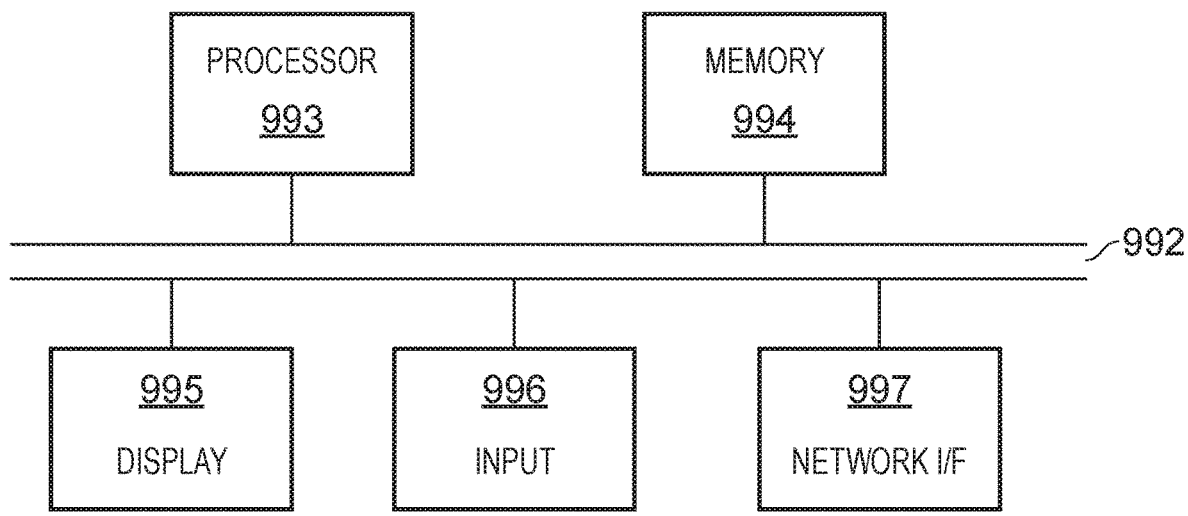
FIG. 22 is a diagram of hardware which is suitable to implement the embodiments.

FIG. 22 is a block diagram of a computing device, such as a data storage server, and which may be used to implement a method of an embodiment of a computer-implemented method to identify healthcare resources used by a patient of a medical institution. The computing device comprises a processor 993, and memory, 994. Optionally, the computing device also includes a network interface 997 for communication with other computing devices, for example with other computing devices of embodiments.

For example, an embodiment may be composed of a network of such computing devices. Optionally, the computing device also includes one or more input mechanisms such as keyboard and mouse 996, and a display unit such as one or more monitors 995. The components are connectable to one another via a bus 992.

The memory 994 may include a computer readable medium, which term may refer to a single medium or multiple media (e.g., a centralized or distributed database and/or associated caches and servers) configured to carry computer-executable instructions or have data structures stored thereon. Computer-executable instructions may include, for example, instructions and data accessible by and causing a general purpose computer, special purpose computer, or special purpose processing device (e.g., one or more processors) to perform one or more functions or operations. Thus, the term "computer-readable storage medium" may also include any medium that is capable of storing, encoding or carrying a set of instructions for execution by the machine and that cause the machine to perform any one or more of the methods of the present disclosure. The term "computer-readable storage medium" may accordingly be taken to include, but not be limited to, solid-state memories, optical media and magnetic media. By way of example, and not limitation, such computer-readable media may include non-transitory computer-readable storage media, including Random Access Memory (RAM), Read-Only Memory (ROM), Electrically Erasable Programmable Read-Only Memory (EEPROM), Compact Disc Read-Only Memory (CD-ROM) or other optical disk storage, magnetic disk storage or other magnetic storage devices, flash memory devices (e.g., solid state memory devices).

The processor 993 is configured to control the computing device and execute processing operations, for example executing code stored in the memory to implement the various different functions of modules described here and in the claims. The memory 994 stores data being read and written by the processor 993. As referred to herein, a processor may include one or more general-purpose processing devices such as a microprocessor, central processing unit, or the like. The processor may include a complex instruction set computing (CISC) microprocessor, reduced instruction set computing (RISC) microprocessor, very long instruction word (VLIW) microprocessor, or a processor implementing other instruction sets or processors implementing a combination of instruction sets. The processor may also include one or more special-purpose processing devices such as an application specific integrated circuit (ASIC), a field programmable gate array (FPGA), a digital signal processor (DSP), network processor, or the like. In one or more embodiments, a processor is configured to execute instructions for performing the operations and steps discussed herein.

The display unit 997 may display a representation of data stored by the computing device, such as the HCRU KG, or part thereof, or the PCO or part thereof and may also display a cursor and dialog boxes and screens enabling interaction between a user and the programs and data stored on the computing device. The input mechanisms 996 may enable a user to input data and instructions to the computing device. For example it can allow a clinician to enter or amend the seed terms used for medical services and healthcare resources.

The network interface (network I/F) 997 may be connected to a network, such as the Internet, and is connectable to other such computing devices via the network, for example to access open data. The network I/F 997 may control data input/output from/to other apparatus via the network. Other peripheral devices such as microphone, speakers, printer, power supply unit, fan, case, scanner, trackerball etc may be included in the computing device.

The HCRU KG builder may comprise processing instructions stored on a portion of the memory 994, the processor 993 to execute the processing instructions, and a portion of the memory 994 to store the data making up the HCRU KG during the execution of the processing instructions. The HCRU KG may be stored on the memory 994 and/or on a connected storage unit.

The HCRU KG customizer may comprise processing instructions stored on a portion of the memory 994, the processor 993 to execute the processing instructions, and a portion of the memory 994 to store data contributing to the customized subgraph during the execution of the processing instructions. The customized subgraph may be stored on the memory 994 and/or on a connected storage unit.

The patient HCRU engine may comprise processing instructions stored on a portion of the memory 994, the processor 993 to execute the processing instructions, and a portion of the memory 994 to store data making up the enriched PCO during the execution of the processing instructions. The enriched PCO may be stored on the memory 994 and/or on a connected storage unit.

The impact estimator may comprise processing instructions stored on a portion of the memory 994, the processor 993 to execute the processing instructions, and a portion of the memory 994 to store data making up the subgraphs during the execution of the processing instructions. The resultant and potentially amended HCRU sub-graph may be stored on the memory 994 and/or on a connected storage unit.

Methods may be carried out on a computing device such as that illustrated in FIG. 22. Such a computing device need not have every component illustrated in FIG. 22, and may be composed of a subset of those components. A method embodying may be carried out by a single computing device in communication with one or more data storage servers via a network. The computing device may be a data storage itself storing the resultant graphs.

A method may be carried out by a plurality of computing devices operating in cooperation with one another. One or more of the plurality of computing devices may be a data storage server storing at least a portion of the graphs.

Advantages

Some of the advantages of the embodiments can be:
It is possible to identify what healthcare resources (and services) a particular patient is using at given point in time (using a PCO enriched with health care resource (and services) information).
It is possible to identify what healthcare resources (and services) are required for a particular diagnosis.
It is possible to estimate the healthcare resources (and services) subgraph given a patient and a potential diagnosis.

Other key benefits can lie in providing a mechanism that allows creation of a healthcare resource utilization knowledge graph, with the support of the clinicians, which is the foundation to identify patient resources utilization in a more accurate way:

In a nutshell, providing the associated health care resource utilization of a particular patient helps to find the best sources of support, as well making decisions about the future. For example, particular embodiments of the can:
Identify group of patients that are using similar healthcare resources, and in this way what health care resources are mostly used in a particular hospital.
Once we have a new patient we can classify him/her in one these groups and estimate what resources he/she will be using.
The hospital will know what healthcare resources need more attention given the patients the hospital has.
Moreover, some solutions are able to detect the potential impact of particular diagnosis for the patients, estimating in this way the resources he/she is going to use. This could be expanded to a whole group of patients, for overall scheduling of resources in a hospital information system.

Brief Description of Technical Terms Used

Health Care Utilization: The measure of the population's use of the health care services available to them. This includes the utilization of Hospital resources, Personal Care Home (PCH) resources, and physician resources. Health care utilization and health status are used to examine how efficiently a health care system produces health in a population.

Health status: An indication of the risk of death of patients based on the type and number of co-morbid conditions or on a number of socio-economic indicators.

Medical treatment: the management and care of a patient, it includes nursing, psychological intervention and specialist mental health rehabilitation.

Diagnosis: the process of determining by examination the nature and circumstance of a disease condition from its signs and symptoms Drugs: something that treats or prevents or alleviates the symptoms of a disease.

Health care services means the furnishing of medicine, medical or surgical treatment, nursing, hospital service, dental service, optometrical service, complementary health services or any or all of the enumerated services or any other necessary services of like character, whether or not contingent upon sickness or personal injury, as well as the furnishing to any person of any and all other services and goods for the purpose of preventing, alleviating, curing or healing human illness, physical disability or injury.

Health resources are all materials, personnel, facilities, funds, and anything else that can be used for providing health care and services.

What is claimed is:

1. A computer apparatus to identify healthcare resources used by a patient, the computer apparatus comprising:
   one or more input mechanisms enabling a user to enter input data and instructions, a display, and a memory storing computer-readable instructions for execution by a processor, the processor configured by the computer-readable instructions to,
   implement a healthcare resource utilization information (HCRU) knowledge graph (KG) builder, a HCRU customizer, and a patient HCRU engine,
   the HCRU KG builder is to input open data and clinician information, to generate a set of medical services terms and a set of medical resources terms from the open data and clinician information, and to associate the medical resources with the medical services to build a HCRU KG;
   the HCRU KG customizer is to,
   perform a matching of the HCRU KG with electronic logs of a medical institution to provide a customized subgraph of the HCRU KG corresponding to the medical institution, an electronic log among the electronic logs being a time stamped record of named activities created from electronic healthcare records,
   the matching includes using the electronic logs of the medical institution to identify services of the medical institution that are represented in the HCRU KG, to filter out services in the HCRU KG that are not provided in the medical institution, to identify resources used from medical institution data and to remove resources from the HCRU KG that are not available in the medical institution, and to apply a graph mining process to the HCRU KG to discover how resources are used in the medical institution; and the patient HCRU engine is to input an initial patient clinical object (PCO) corresponding to the patient, which represents information about clinical history, diagnoses, risks, treatments, symptoms, and drugs, of the patient in a form of a graph, to associate and annotate the initial PCO with previous HCRU from the customized subgraph of the HCRU KG to provide an enriched PCO that, by the association and annotation with the customized subgraph of the HCRU KG, includes the previous HCRU of the patient to represent a HCRU subgraph of the patient as a patient HCRU subgraph;

implement an impact estimator to, receive potential diagnosis information from a clinician;

identify and extract potential healthcare resources and services in the customized subgraph of the HCRU KG associated with the potential diagnosis to form a HCRU subgraph associated with the potential diagnosis; and perform graph analysis on the HCRU subgraph associated with the potential diagnosis and the patient HCRU subgraph to obtain an updated patient HCRU subgraph for the patient taking the potential diagnosis into account; and cause the display to display a representation of the customized subgraph of HCRU KG or part thereof and to display the PCO or part thereof and the updated patient HCRU subgraph created by the impact estimator, and also to display a cursor and dialog boxes and screens enabling interaction between the impact estimator and the user via the input mechanisms.

2. A computer apparatus according to claim 1, wherein: the impact estimator applies a graph mining process to the HCRU subgraph to estimate how the HCRU subgraph associated with the potential diagnosis will affect the patient HCRU subgraph.

3. A computer apparatus according to claim 1, wherein: vertices in the updated patient HCRU subgraph associated with the potential diagnosis are provided with scores related to a probability of resource utilization and use of the medical services.

4. A computer apparatus according to claim 1, wherein: the impact estimator is to receive information indicating healthcare resources potentially used by a population of patients of a medical institution and to receive PCOs for the population and a plurality of obtained updated patient HCRU subgraphs are used to estimate potential healthcare resource utilization across the population.

5. A computer apparatus according to claim 1, wherein: the enriched PCO is provided as a graph centered on an identification (ID) of the patient in form of a patient ID vertex, with edges linking the patient ID vertex to vertices representing clinical data, and to vertices representing resource utilization and medical services as the patient HCRU subgraph.

6. A computer apparatus according to claim 1, wherein: the initial PCO is limited to nodes related to one or more of: a condition, an episode of the condition, a timeframe of the condition, and an actual diagnosis of the condition.

7. A computer apparatus according to claim 1, wherein: the potential diagnosis information includes an actual diagnosis and relations of the actual diagnosis to symptoms, drugs, and treatments.

8. A computer apparatus according to claim 1, wherein to build the HCRU KG, the HCRU KG builder is to, collect seeds for an initial set of medical services terms and for an initial set of medical resources terms from the clinician information;

reconcile initial sets of the terms from clinician with the open data to provide an enhanced set of terms proposed by the clinicians and annotated using the open data;

create two models, a first model representing healthcare resources and a second model representing healthcare services; and create relations between the two models, using relation mining in the open data, scoring the relations according to a number of occurrences of the relations in the open data.

9. A computer apparatus according to claim 1, wherein the HCRU KG customizer is to, input the electronic medical institution logs and internal regulations of the medical institution, extract process knowledge from the electronic medical institution logs, and project the extracted process knowledge onto the internal regulations of the medical institution to check whether the extracted process knowledge conforms to the internal regulations of the medical institution.

10. A computer apparatus according to claim 1, wherein: the patient HCRU engine is to use clinical data present in the initial PCO and to add links to new vertices representing healthcare resources using the customized subgraph of the HCRU KG as a template.

11. A computer-implemented method comprising:

receiving open data and clinician information, to generate a set of medical services terms and a set of medical resources terms from the open data and clinician information, and to associate the medical resources with the medical services to build a HCRU KG;

perform a matching of the HCRU KG with electronic logs of a medical institution to provide a customized subgraph of the HCRU KG corresponding to the medical institution, an electronic log among the electronic logs being a time stamped record of named activities created from electronic healthcare records, the matching including using the electronic logs of the medical institution to identify services of the medical institution that are represented in the HCRU KG, to filter out services in the HCRU KG that are not provided in the medical institution, to identify resources used from medical institution data and to remove resources from the HCRU KG that are not available in the medical institution, and to apply a graph mining process to the HCRU KG to discover how resources are used in the medical institution;

receiving an initial patient clinical object (PCO) corresponding to the patient, which represents information about clinical history, diagnoses, risks, treatments, symptoms, and drugs, of the patient in a form of a graph, to associate and annotate the initial PCO with previous HCRU from the customized subgraph of the HCRU KG to provide an enriched PCO that, by the association and annotation with the customized subgraph of the HCRU KG, includes the previous HCRU of the patient to represent a HCRU subgraph of the patient as a patient HCRU subgraph;

receiving potential diagnosis information from a clinician;

identifying and extracting potential healthcare resources and services in the customized subgraph of the HCRU KG associated with the potential diagnosis to form a HCRU subgraph associated with the potential diagnosis;

performing graph analysis on the HCRU subgraph associated with the potential diagnosis and the patient HCRU subgraph to obtain an updated patient HCRU subgraph for the patient taking the potential diagnosis into account; and displaying information indicating a representation of the customized subgraph of the HCRU KG or part thereof and of the PCO or part thereof and of the updated patient HCRU subgraph, and displaying a cursor and dialog boxes and screens enabling user interaction with the displayed information.

12. A non-transitory computer-readable medium storing a computer program which when executed on a computer carries out a method comprising:

receiving open data and clinician information, to generate a set of medical services terms and a set of medical resources terms from the open data and clinician information, and to associate the medical resources with the medical services to build a HCRU KG;

perform a matching of the HCRU KG with electronic logs of a medical institution to provide a customized subgraph of the HCRU KG corresponding to the medical institution, an electronic log among the electronic logs being a time stamped record of named activities created from electronic healthcare records, the matching including using the electronic logs of the medical institution to identify services of the medical institution that are represented in the HCRU KG, to filter out services in the HCRU KG that are not provided in the medical institution, to identify resources used from medical institution data and to remove resources from the HCRU KG that are not available in the medical institution, and to apply a graph mining process to the HCRU KG to discover how resources are used in the medical institution;

receiving an initial patient clinical object (PCO) corresponding to the patient, which represents information about clinical history, diagnoses, risks, treatments, symptoms, and drugs, of the patient in a form of a graph, to associate and annotate the initial PCO with previous HCRU from the customized subgraph of the HCRU KG to provide an enriched PCO that, by the association and annotation with the customized subgraph of the HCRU KG, includes the previous HCRU of the patient to represent a HCRU subgraph of the patient as a patient HCRU subgraph;

receiving potential diagnosis information from a clinician;

identifying and extracting potential healthcare resources and services in the customized subgraph of the HCRU KG associated with the potential diagnosis to form a HCRU subgraph associated with the potential diagnosis;

performing graph analysis on the HCRU subgraph associated with the potential diagnosis and the patient HCRU subgraph to obtain an updated patient HCRU subgraph for the single patient taking the potential diagnosis into account; and displaying information indication a representation of the customized subgraph of the HCRU KG or part thereof and of the PCO or part thereof and of the updated patient HCRU subgraph, and displaying a cursor and dialog boxes and screens enabling user interaction with the displayed information.

* * * * *